US011298199B2

(12) United States Patent
Ogawa et al.

(10) Patent No.: US 11,298,199 B2
(45) Date of Patent: Apr. 12, 2022

(54) MANIPULATOR SYSTEM AND METHOD FOR RESTRICTING A RETREATING MOTION OF A MANIPULATOR ACCORDING TO A PROTRUSION STATE OF A MANIPULATOR JOINT

(71) Applicant: OLYMPUS CORPORATION, Tokyo (JP)

(72) Inventors: Ryohei Ogawa, Tokyo (JP); Keigo Takahashi, Tokyo (JP); Kosuke Kishi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 593 days.

(21) Appl. No.: 16/110,586

(22) Filed: Aug. 23, 2018

(65) Prior Publication Data
US 2018/0360551 A1 Dec. 20, 2018

Related U.S. Application Data

(63) Continuation of application No. PCT/JP2016/055710, filed on Feb. 25, 2016.

(51) Int. Cl.
A61B 1/00 (2006.01)
A61B 1/005 (2006.01)
(Continued)

(52) U.S. Cl.
CPC .......... *A61B 34/37* (2016.02); *A61B 1/0002* (2013.01); *A61B 1/00006* (2013.01);
(Continued)

(58) Field of Classification Search
None
See application file for complete search history.

(56) References Cited

U.S. PATENT DOCUMENTS 7,974,681 B2 * 7/2011 Wallace ................ A61B 90/50
600/424
2003/0033024 A1 2/2003 Sunaoshi
(Continued)

FOREIGN PATENT DOCUMENTS

EP 1728462 A2 12/2006
EP 2014218 A2 1/2009
(Continued)

OTHER PUBLICATIONS

Office Action dated Apr. 9, 2020 received in U.S. Appl. No. 16/011,163.
(Continued)

Primary Examiner — Michael J Carey
Assistant Examiner — Minqiao Huang
(74) Attorney, Agent, or Firm — Scully, Scott, Murphy & Presser, P.C.

(57) ABSTRACT

A manipulator system includes: a manipulator including an elongated flexible section, a movable section provided at a distal end of the flexible section, and a driver that is provided at a proximal end of the flexible section and that drives the movable section; an insertion section having a channel into which the manipulator is inserted; an advancing/retreating section that advances/retreats the manipulator and that causes the movable section of the manipulator to protrude from, and to be withdrawn into, a distal end of the channel; a protrusion-state acknowledgement section that acknowledges a protrusion state in which an entirety of the movable section protrudes from the distal end of the channel; and a restricting section that, when the protrusion state is acknowledged with the protrusion-state acknowledgement section, restricts further retreating motion of the driver performed by the advancing/retreating section.

22 Claims, 19 Drawing Sheets

(51) Int. Cl.
      *A61B 1/008*     (2006.01)
      *A61B 34/37*     (2016.01)
      *B25J 3/00*      (2006.01)
      *A61B 90/00*     (2016.01)
      *B25J 19/06*     (2006.01)
      *A61B 34/30*     (2016.01)
      *A61B 34/00*     (2016.01)
      *A61B 34/20*     (2016.01)

(52) U.S. Cl.
     CPC ............ *A61B 1/008* (2013.01); *A61B 1/0016* (2013.01); *A61B 1/00045* (2013.01); *A61B 1/0057* (2013.01); *A61B 1/00057* (2013.01); *A61B 1/00149* (2013.01); *A61B 34/30* (2016.02); *A61B 90/00* (2016.02); *B25J 3/00* (2013.01); *B25J 19/06* (2013.01); *A61B 34/70* (2016.02); *A61B 2034/2061* (2016.02); *A61B 2034/301* (2016.02); *A61B 2090/061* (2016.02)

(56) References Cited

U.S. PATENT DOCUMENTS

| | | | |
|---|---|---|---|
| 2003/0135203 A1 | 7/2003 | Wang et al. | |
| 2005/0234293 A1* | 10/2005 | Yamamoto | A61B 90/57 600/102 |
| 2006/0100610 A1* | 5/2006 | Wallace | A61B 8/4254 606/1 |
| 2006/0258905 A1* | 11/2006 | Kaji | A61B 1/018 600/106 |
| 2006/0276784 A1 | 12/2006 | Miyajima et al. | |
| 2007/0043338 A1* | 2/2007 | Moll | A61B 17/062 606/1 |
| 2007/0088354 A1 | 4/2007 | Sugita | |
| 2007/0135803 A1* | 6/2007 | Belson | A61B 5/064 606/1 |
| 2007/0250074 A1* | 10/2007 | Brock | A61B 34/71 606/130 |
| 2008/0183193 A1 | 7/2008 | Omori et al. | |
| 2008/0188868 A1 | 8/2008 | Weitzner et al. | |
| 2008/0188869 A1 | 8/2008 | Weitzner et al. | |
| 2008/0188871 A1 | 8/2008 | Smith et al. | |
| 2008/0188890 A1 | 8/2008 | Weitzner et al. | |
| 2008/0193260 A1 | 8/2008 | Yokokohji et al. | |
| 2008/0221391 A1 | 9/2008 | Weitzner et al. | |
| 2008/0243176 A1 | 10/2008 | Weitzner et al. | |
| 2009/0018390 A1 | 1/2009 | Honda et al. | |
| 2009/0112060 A1* | 4/2009 | Sugiyama | A61B 1/2736 600/104 |
| 2009/0143642 A1* | 6/2009 | Takahashi | A61B 1/018 600/106 |
| 2009/0275798 A1 | 11/2009 | Naito | |
| 2009/0326319 A1 | 12/2009 | Takahashi et al. | |
| 2010/0318100 A1* | 12/2010 | Okamoto | A61B 34/71 606/130 |
| 2010/0331856 A1* | 12/2010 | Carlson | A61B 34/30 606/130 |
| 2012/0004502 A1 | 1/2012 | Weitzner et al. | |
| 2012/0143353 A1 | 6/2012 | Kishi | |
| 2012/0191247 A1 | 7/2012 | Kishi | |
| 2014/0005683 A1 | 1/2014 | Stand et al. | |
| 2014/0148817 A1 | 5/2014 | Hasegawa et al. | |
| 2014/0246471 A1 | 9/2014 | Jaworek et al. | |
| 2014/0246472 A1 | 9/2014 | Kimsey et al. | |
| 2014/0246473 A1 | 9/2014 | Auld | |
| 2014/0246474 A1 | 9/2014 | Hall et al. | |
| 2014/0246475 A1 | 9/2014 | Hall et al. | |
| 2014/0246476 A1* | 9/2014 | Hall | A61B 17/32002 227/175.1 |
| 2014/0246477 A1 | 9/2014 | Levy et al. | |
| 2014/0246478 A1 | 9/2014 | Baber et al. | |
| 2014/0246479 A1 | 9/2014 | Baber et al. | |
| 2014/0246777 A1 | 9/2014 | Levy et al. | |
| 2014/0249557 A1 | 9/2014 | Koch, Jr. et al. | |
| 2015/0238180 A1 | 8/2015 | Weitzner et al. | |
| 2015/0313449 A1 | 11/2015 | Stand et al. | |
| 2016/0089007 A1 | 3/2016 | Weitzner et al. | |
| 2016/0228113 A1 | 8/2016 | Weitzner et al. | |
| 2016/0324589 A1* | 11/2016 | Ogawa | A61B 34/74 |
| 2017/0007345 A1 | 1/2017 | Smith et al. | |
| 2017/0007347 A1 | 1/2017 | Jaworek et al. | |
| 2017/0265953 A1* | 9/2017 | Fenech | A61B 34/30 |
| 2019/0231466 A1 | 8/2019 | Weitzner et al. | |

FOREIGN PATENT DOCUMENTS

| | | |
|---|---|---|
| EP | 2113187 A1 | 11/2009 |
| EP | 2116174 A1 | 11/2009 |
| EP | 2617530 A1 | 7/2013 |
| EP | 2639018 A1 | 9/2013 |
| EP | 2 772 196 A2 | 9/2014 |
| EP | 2 772 204 A2 | 9/2014 |
| EP | 2 772 205 A1 | 9/2014 |
| EP | 2 772 206 A2 | 9/2014 |
| EP | 2 772 207 A2 | 9/2014 |
| EP | 2 772 208 A1 | 9/2014 |
| EP | 2 772 209 A1 | 9/2014 |
| EP | 2 772 210 A2 | 9/2014 |
| EP | 2 772 211 A2 | 9/2014 |
| EP | 2 772 214 A2 | 9/2014 |
| EP | 3108845 A1 | 12/2016 |
| EP | 3 449 850 A1 | 3/2019 |
| JP | H08011071 A | 1/1996 |
| JP | 2001310277 A | 11/2001 |
| JP | 2005131417 A | 5/2005 |
| JP | 2005305585 A | 11/2005 |
| JP | 2006326157 A | 12/2006 |
| JP | 2006334695 A | 12/2006 |
| JP | 2007111148 A | 5/2007 |
| JP | 2008212349 A | 9/2008 |
| JP | 2009011809 A | 1/2009 |
| JP | 2009268592 A | 11/2009 |
| JP | 2012040202 A | 3/2012 |
| JP | 2012131014 A | 7/2012 |
| JP | 2012148379 A | 8/2012 |
| JP | 5198014 B2 | 5/2013 |
| JP | 2014500152 A | 1/2014 |
| JP | 2015154895 A | 8/2015 |
| WO | 2008/070556 A1 | 6/2008 |
| WO | 2012054829 A2 | 4/2012 |
| WO | 2016/018618 A1 | 2/2016 |

OTHER PUBLICATIONS

Supplementary Partial European Search Report dated Sep. 4, 2019 received in EP 16 89 1497.6.

International Search Report dated Apr. 26, 2016 issued in PCT/JP2016/055710.

International Search Report dated Apr. 26, 2016 issued in PCT/JP2016/055717.

* cited by examiner

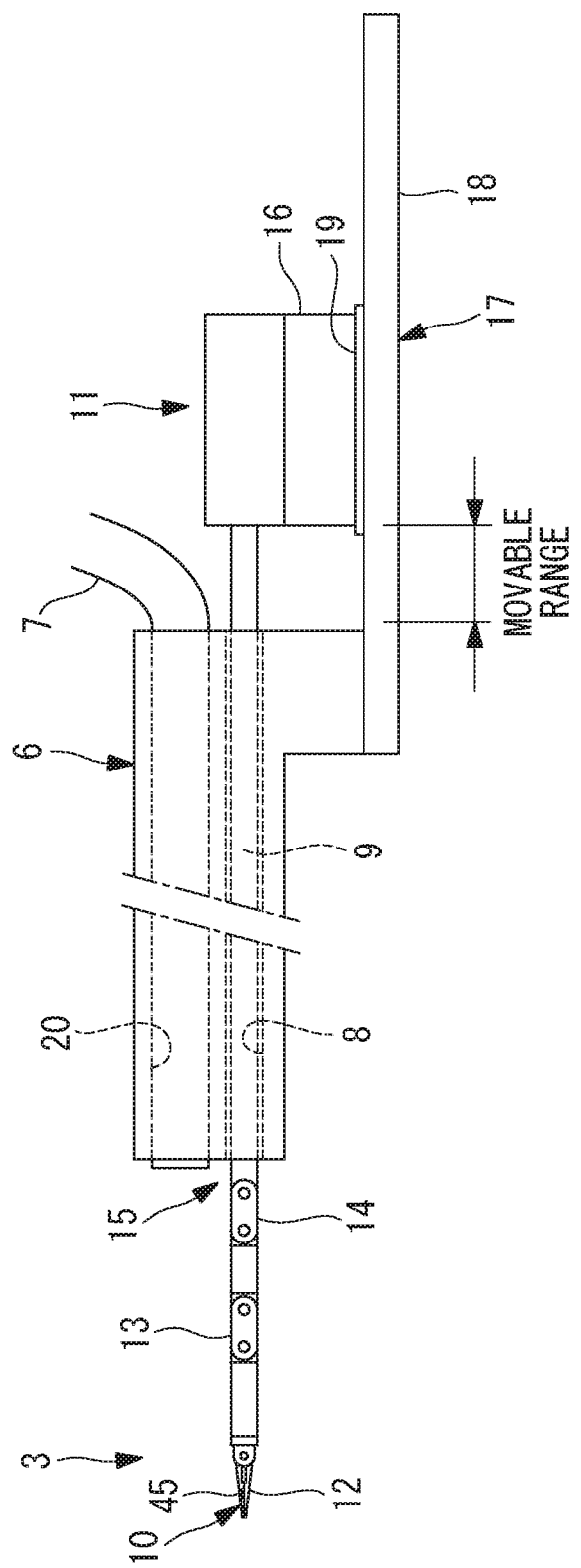

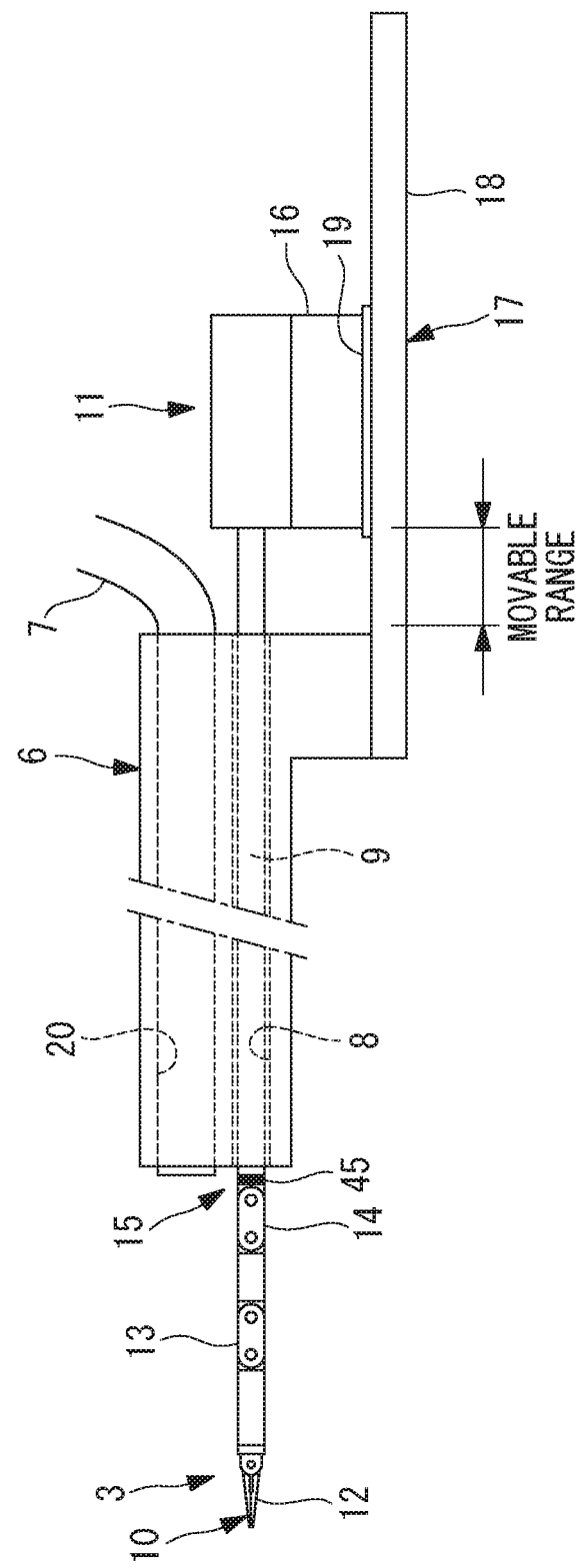

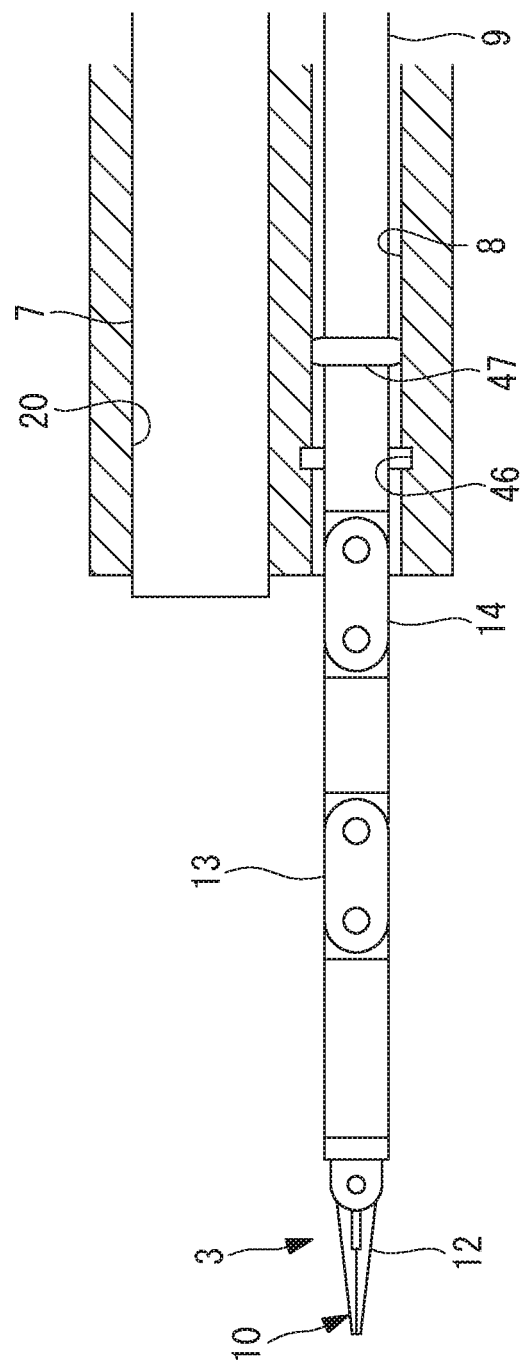

```
Set Position of projection

Adjust rolling axis and
push the "OK" button
after confirmation of
all joints on screen.
```

OK

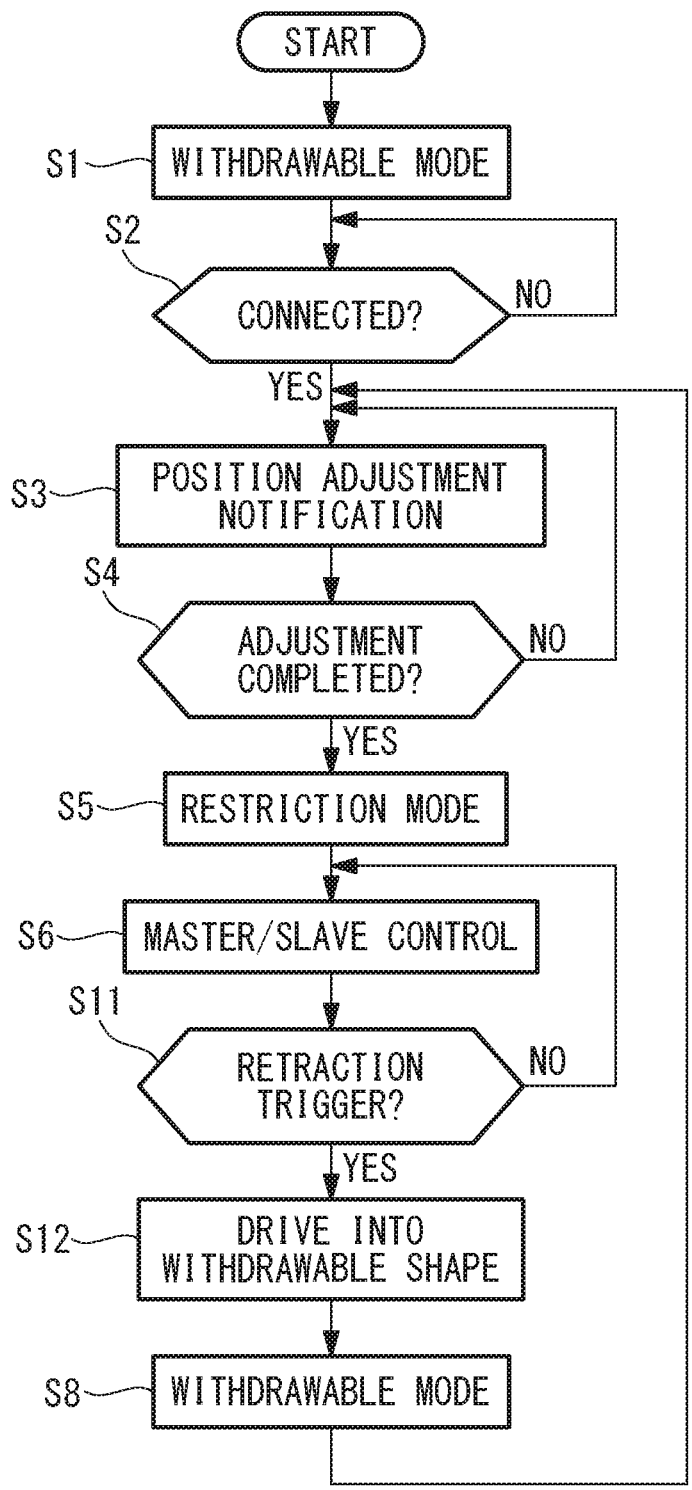

MANIPULATOR SYSTEM AND METHOD FOR RESTRICTING A RETREATING MOTION OF A MANIPULATOR ACCORDING TO A PROTRUSION STATE OF A MANIPULATOR JOINT

CROSS-REFERENCE TO RELATED APPLICATIONS

This is a continuation of International Application PCT/JP2016/55710, with an international filing date of Feb. 25, 2016, which is hereby incorporated by reference herein in its entirety.

TECHNICAL FIELD

The present invention relates to a manipulator system and a method for operating the same.

BACKGROUND ART

There is a well-known manipulator system that has a multiple-joint treatment tool and that employs a master/slave method (refer to, for example, Patent Literature 1). In this manipulator system, the position of the manipulator protruding from the distal end of a forceps channel provided in an insertion section is detected, and the angles of the joints are determined so that the manipulator portion disposed in the forceps channel takes a shape according to the shape of the forceps channel.

CITATION LIST

Patent Literature

{PTL 1}
Japanese Unexamined Patent Application, Publication No. 2008-212349

SUMMARY OF INVENTION

One aspect of the present invention is directed to a manipulator system including: a manipulator including an elongated flexible section, a movable section provided at a distal end of the flexible section, and a driver that is provided at a proximal end of the flexible section and that drives the movable section; an insertion section having a channel into which the manipulator is inserted; an advancing/retreating section that advances/retreats the manipulator and that causes the movable section of the manipulator to protrude from, and to be withdrawn into, a distal end of the channel; a protrusion-state acknowledgement section that acknowledges a protrusion state in which an entirety of the movable section protrudes from the distal end of the channel; and a restricting section that, when the protrusion state is acknowledged with the protrusion-state acknowledgement section, restricts further retreating motion of the driver performed by the advancing/retreating section.

Another aspect of the present invention is directed to a method for operating a manipulator system, the method including: a state acknowledgement step of acknowledging, in a state where a manipulator including a movable section at a distal end of an elongated flexible section and a drive unit, at a proximal end thereof, for driving the movable section is inserted in a channel of an insertion section in which a curved shape is set and that has flexibility, whether or not a protrusion state in which an entirety of the movable section protrudes from a distal end of the channel is achieved; and a restriction step of restricting a retreating motion of the driver from the position thereof when it is acknowledged in the state acknowledgement step that the protrusion state is achieved.

Another aspect of the present invention is directed to a controller for controlling a manipulator system that includes a manipulator having a movable section provided at a distal end, a tube into which the manipulator is insertable, and a slider to which the manipulator is attachable, the manipulator system causing the movable section to protrude from, and to be withdrawn into, the tube by advancing/retreating the slider, wherein the controller performs an acknowledgement of a protrusion state in which an entirety of the movable section protrudes from the tube, and wherein, when a position of the slider at the time of performing the acknowledgement is regarded as a restricting position, the controller controls the slider in such a way that a retreating motion of the slider is restricted when the slider is retreated to the restricting position.

BRIEF DESCRIPTION OF DRAWINGS

FIG. 5A is a side elevational view showing a state where the entire movable section of a manipulator of the manipulator system in FIG. 1 protrudes from a distal end of an overtube.

FIG. 10A is a partial longitudinal sectional view showing a modification of a state recognition section of the manipulator system in FIG. 1.

FIG. 10B is a partial longitudinal sectional view showing a modification of the state recognition section of the manipulator system in FIG. 10A.

FIG. 15 is a flowchart for illustrating another modification of the method for operating the manipulator system in FIG. 9.

DESCRIPTION OF EMBODIMENTS

A manipulator system 1 according to one embodiment of the present invention and a method for operating the same will now be described with reference to the drawings.

Figure 1:
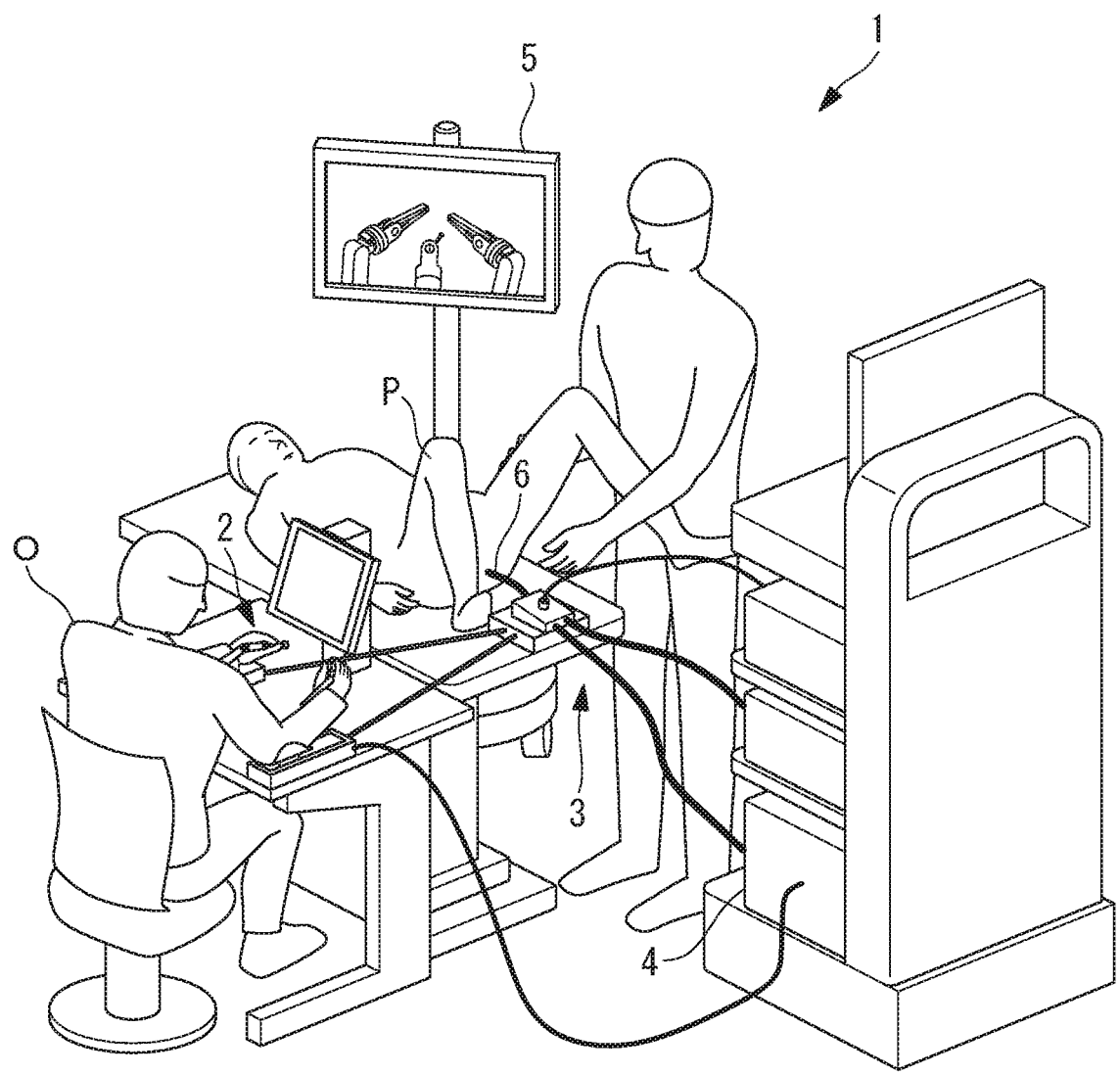
FIG. 1 is an overall configuration diagram showing a manipulator system according to one embodiment of the present invention.
Figure 2:
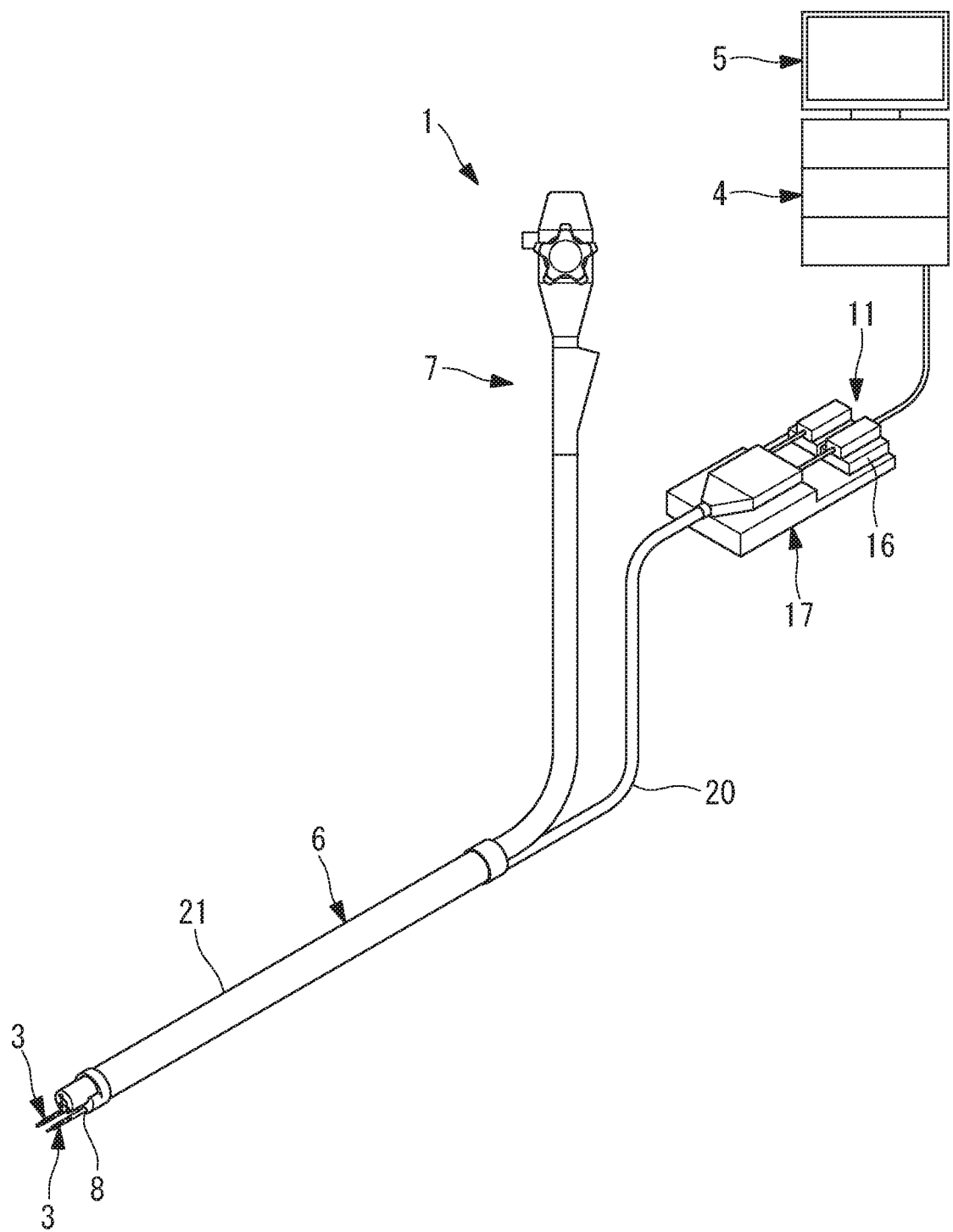
FIG. 2 is a perspective view showing a part of the manipulator system in FIG. 1.

As shown in FIGS. 1 and 2, the manipulator system 1 according to this embodiment includes: operation input sections 2 operated by an operator O; an overtube (insertion section) 6 inserted into the body cavity of a patient P; manipulators 3 inserted into channels 8 of the overtube 6 and an endoscope (image acquisition unit) 7; a control unit 4 for controlling the manipulators 3 on the basis of the operation of the operation input sections 2; and a monitor (display unit) 5. Although two manipulators 3 are provided and are inserted into two respective channels 8 of the overtube 6 in the example shown in FIG. 2, one of the manipulators 3 will be described below.

Figure 3:
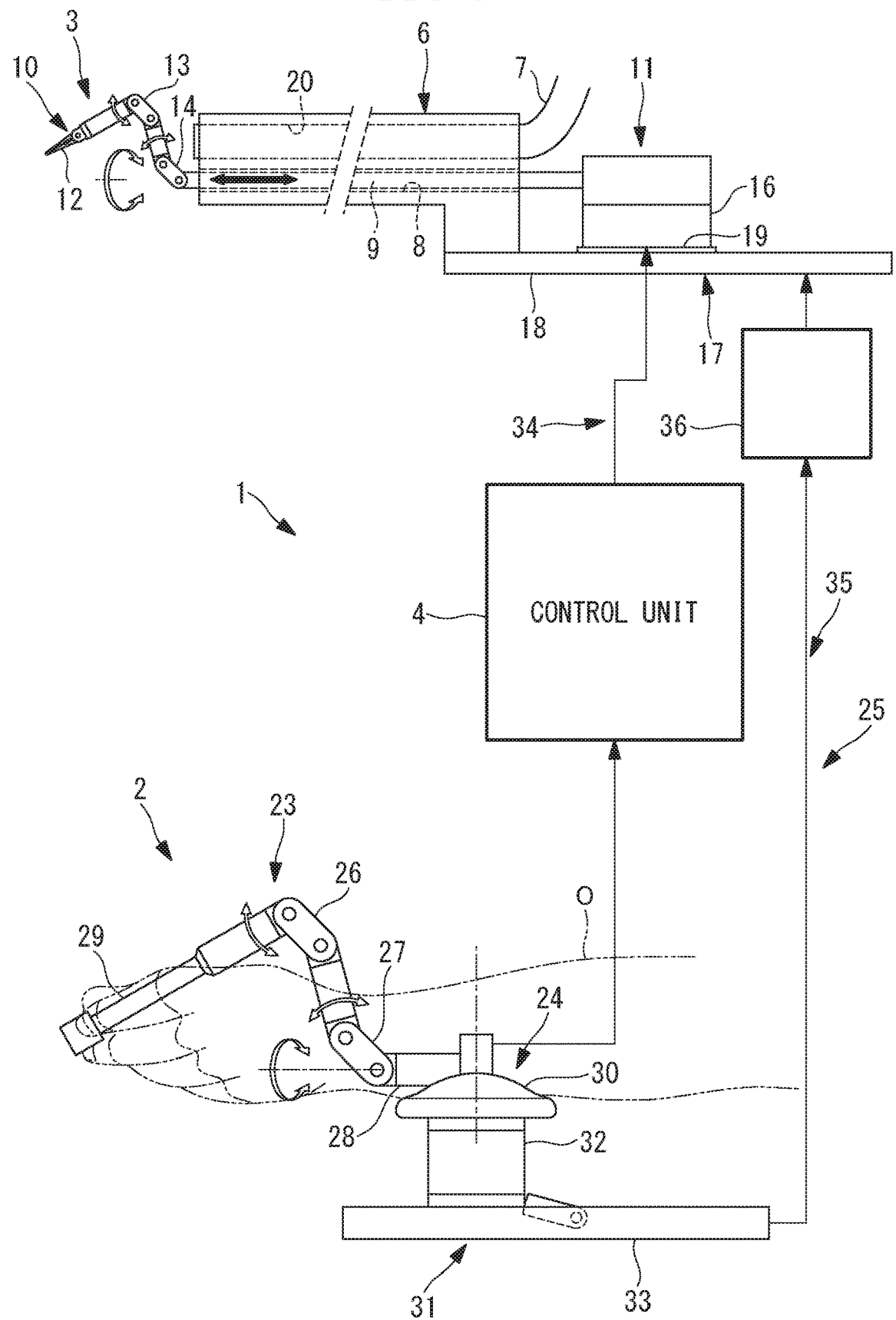
FIG. 3 is a diagram showing a manipulator, an operation input section, and a control unit used in the manipulator system in FIG. 1.

As shown in FIG. 3, the manipulator 3 includes: an elongated flexible section 9 inserted into the body of the patient P via a channel 8 of the overtube 6; a movable section 10 provided at the distal end of the flexible section 9; and a drive unit 11 that is disposed on the proximal end side of the insertion section 6 and that drives the movable section 10 with a force transmission member, such as a wire, not shown in the figure.

The movable section 10 includes: a treatment section 12 that is disposed at the most distal end and that acts on an affected area in the body to treat the affected area; and a plurality of joints 13, 14, and 15 for changing the distal position and orientation of the treatment section 12. The treatment section 12 is a gripping forceps, a high frequency knife, or the like.

In addition, as shown in FIG. 3, the manipulator 3 includes: a motor unit 16 that is attachably/detachably connected to the drive unit 11 and that incorporates electric drive sources (not shown in the figure), such as motors, for imparting motive power to the drive unit 11; and an advancing/retreating mechanism (advancing/retreating section) 17 for linearly moving the motor unit 16.

The advancing/retreating mechanism 17 includes: a base 18; and a slider 19 for supporting the motor unit 16 so as to be linearly movable relative to this base 18.

The overtube 6 is a tube formed of a material having flexibility and, as shown in FIGS. 2 and 3, includes: a distal-end-side tubular section 21 having the manipulator channel (channel) 8 for allowing the manipulator 3 to pass therethrough and an endoscope channel 20 for allowing the endoscope 7 to pass therethrough; and a proximal-end-side tubular section 22 extending so as to lengthen the manipulator channel 8 from the proximal end of the distal-end-side tubular section 21 towards the proximal end side.

As shown in FIG. 3, an operation input section 2 includes: a first operating section 23 that is gripped and operated with the hand of the operator O; a second operating section 24 operated with the wrist or the arm of the operator O; and a command transmission section 25 for transmitting, to the manipulator 3, an operating command input by these operating sections 23 and 24.

The first operating section 23 is configured in a shape similar to that of the movable section 10 of the manipulator 3, and a distal end portion 29, supported by the same number of joints 26, 27, and 28 as the number of joints of the movable section 10, is gripped with the hand of the operator O and moved with the palm or the fingers. The first operating section 23 includes a sensor (not shown in the figure) for detecting the angle of each of the joints 26, 27, and 28 constituting the first operating section 23. Note that the shape of the first operating section 23 is not necessarily similar to, but may not be similar to, that of the movable section 10.

The sensors generate electrical signals according to the angles of the respective joints 26, 27, and 28. By doing so, each of the first operating sections 23 allows the operator O to input an operating command with his/her palm or fingers, thereby generating a motion command composed of an electrical signal.

In addition, as described below, the distal end portion 29 of the first operating section 23 includes an input section (not shown in the figure) with which the operator O performs input to confirm that the entire movable section 10 protrudes from the distal end of the manipulator channel 8.

The second operating section 24 includes: an arm rest pedestal 30 fixed to the proximal section of the first operating section 23; and a linear-motion mechanism 31 movably and integrally supporting the arm rest pedestal 30 and the first operating section 23. The arm rest pedestal 30 is disposed at a position at which, when the operator O grips the distal end portion 29 of the first operating section 23, an arm portion near the wrist of the hand gripping the distal end portion 29 rests on the arm rest pedestal 30.

Figure 4:
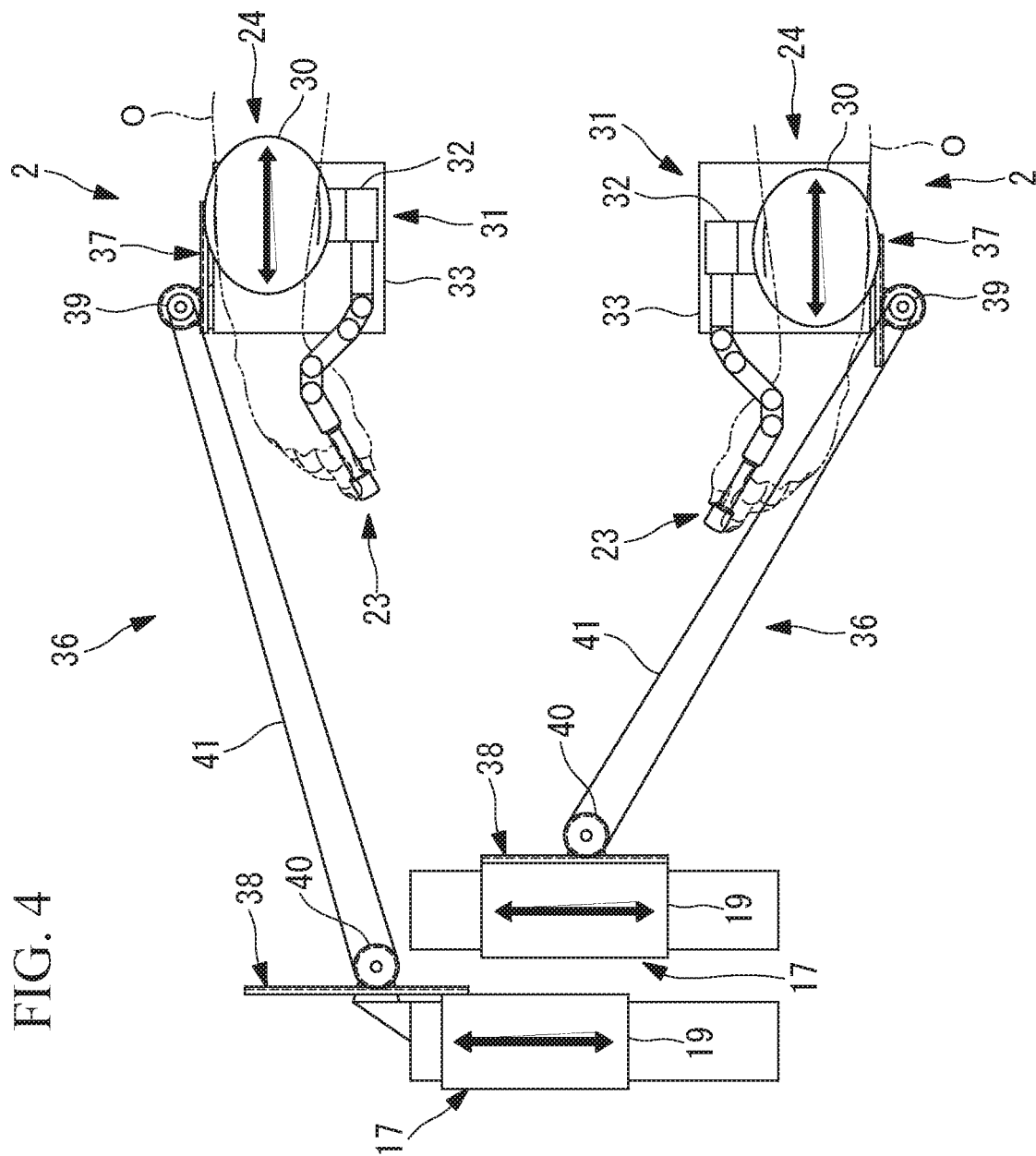
FIG. 4 is a plan view for illustrating second operating sections, a command transmission section, and advancing/retreating mechanisms of operation input sections of the manipulator system in FIG. 1.

The linear-motion mechanism 31 includes: a slider 32 for fixing the arm rest pedestal 30 and the first operating section 23; and a linear guide 33 for supporting the slider 32 so as to be movable in the horizontal direction, as indicated by black arrows in FIGS. 3 and 4. By moving the slider 32 in the horizontal direction by means of the arm resting on the arm rest pedestal 30, the position of the first operating section 23 can be moved while maintaining the position/orientation with which the first operating section 23 is gripped. By doing so, the second operating sections 24 receive operating commands input with the wrists or the arms of the operator O and generate motion commands by using the forces input with the wrists or the arms as mechanical driving forces of the two sliders 32. Note that a method for generating a motion command as an electrical driving force may be employed in addition to the case where a slider 32 generates a motion command as a mechanical driving force.

The command transmission section 25 includes: an electrical signal transmission unit 34 for connecting the first operating section 23 and the drive unit 11; and a mechanical force transmission section 35 for connecting the second operating section 24 and the advancing/retreating mechanism 17.

The electrical signal transmission unit 34 transmits, to the control unit 4, a motion command composed of an electrical signal generated by the first operating section 23 and supplies each motor of the motor unit 16 with a command signal generated by the control unit 4. The control unit 4 calculates the amount of rotational movement and the rotational speed for each motor of the motor unit 16 on the basis of the motion command generated by the first operating section 23, thus controlling each motor.

As shown in FIG. 3, the mechanical force transmission section 35 includes a transmission section 36 for converting a linear motion for moving forward/backward each of the sliders 32 of the operation input sections 2 into a linear motion of the advancing/retreating mechanism 17.

As shown in FIG. 4, a transmission section 36 includes: a first rack and pinion mechanism 37 for converting the amount of linear movement of the slider 32 of the operation input section 2 into a rotational angle; a second rack and pinion mechanism 38 for converting the rotational movement into the amount of linear movement of the slider 19 of the advancing/retreating mechanism 17; pulleys 39 and 40 fixed to the respective pinion gears of these rack and pinion mechanisms 37 and 38; and a belt 41 bridging over these pulleys 39 and 40.

In this embodiment, the motion range of the slider 32 of the linear-motion mechanism 31 corresponds to the motion range of the slider 32 of the advancing/retreating mechanism 17 for moving the manipulator 3 relative to the overtube 6 in the longitudinal direction of the flexible section 9. More specifically, when the slider 32 is moved between the frontmost end position and the rearmost end position, the manipulator 3 can be shifted between a treatment state where the entire movable section 10 provided at the distal end of the manipulator 3 protrudes forward from the manipulator channel 8 of the overtube 6, as shown in FIG. 5A, and an accommodation state where the entire movable section 10 is accommodated in the manipulator channel 8 of the overtube 6, as shown in FIG. 6.

Also in this embodiment, a position-adjustable restricting section 42 for restricting further retreating motion of the slider 19 is provided at a midway position in the motion range of the slider 19 of the advancing/retreating mechanism 17.

Figure 7:
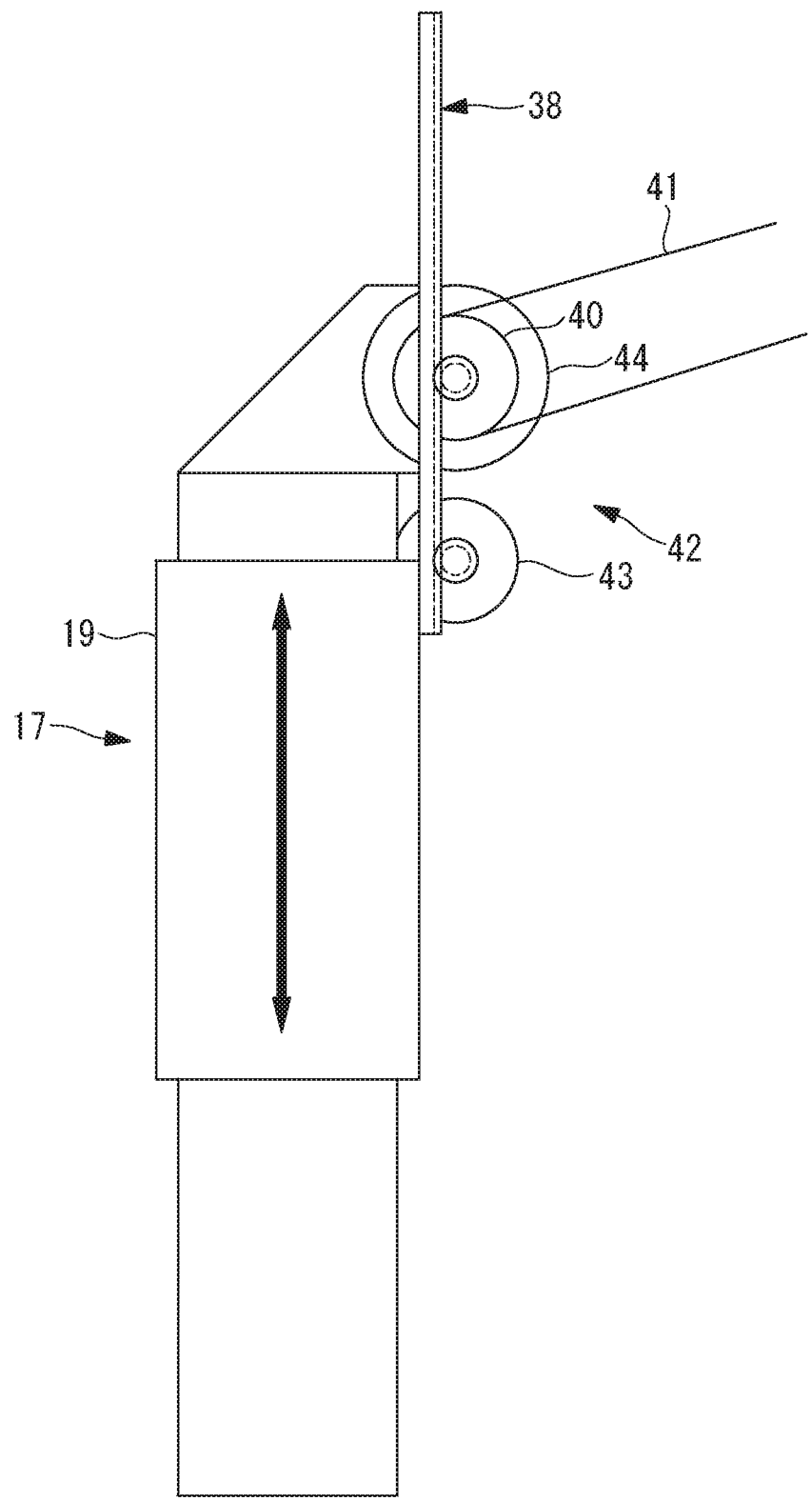
FIG. 7 is a diagram showing one example of a restricting section in the manipulator system in FIG. 1.

As shown in, for example, FIG. 7, the restricting section 42 includes: an encoder 43 for detecting the advance/retreat position of the rack gear of the second rack and pinion mechanism 38; and a brake 44 that restricts the rotation of the pinion gear when this encoder 43 detects a predetermined position.

Figure 5B:
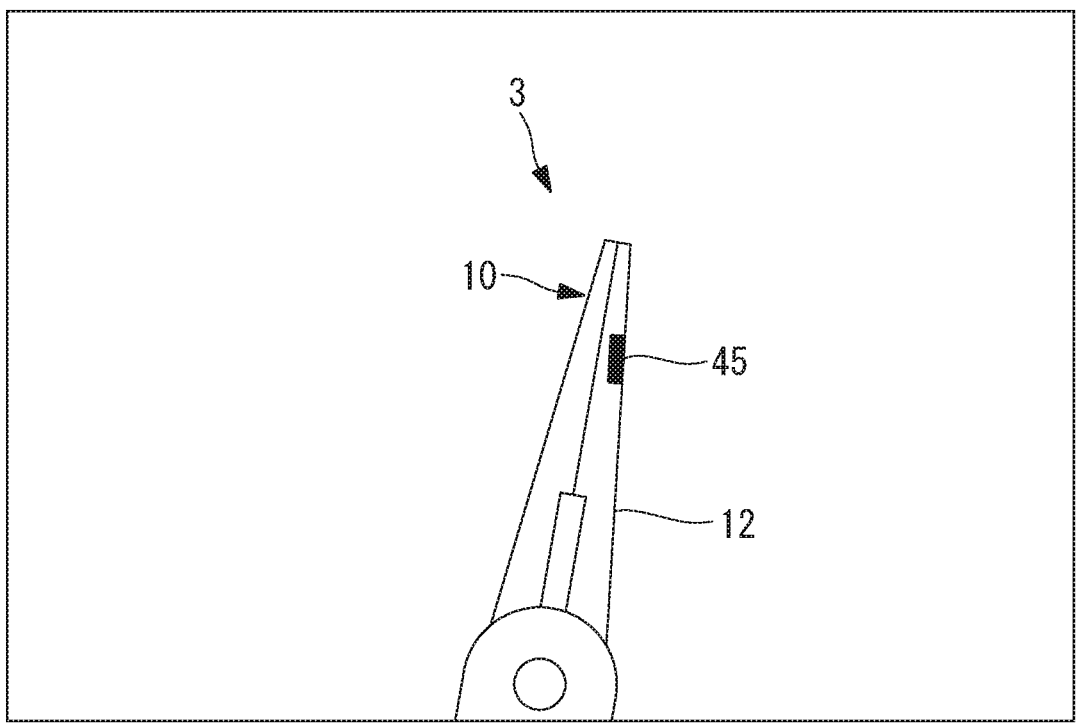
FIG. 5B is a diagram showing one example of an endoscopic image indicating a mark, the image being acquired with the endoscope inserted into the overtube of the manipulator system in FIG. 1.
Figure 6:
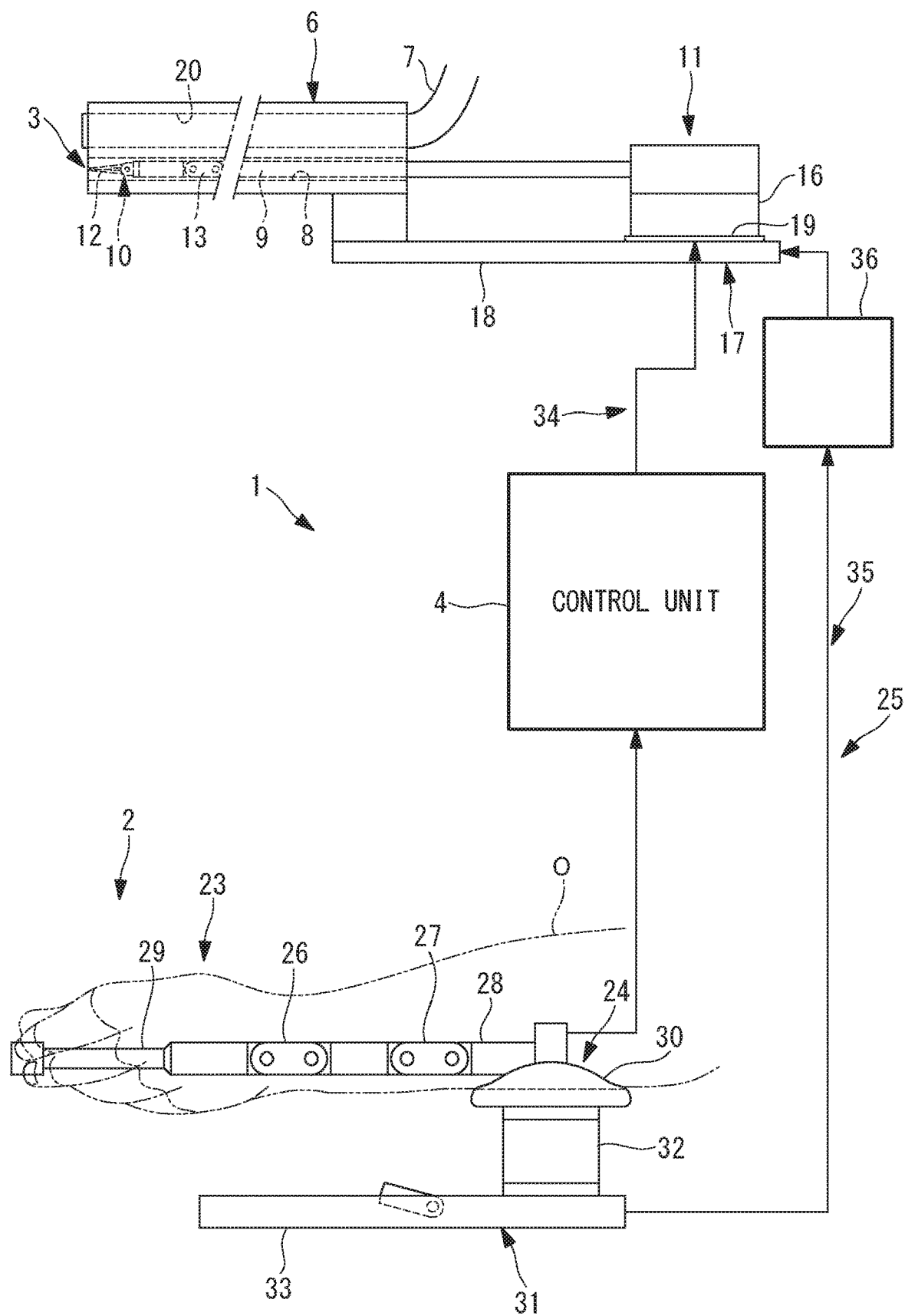
FIG. 6 is a diagram showing an accommodation state in which the entire movable section of the manipulator system in FIG. 1 is accommodated in a manipulator channel of the over tube.

In addition, in this embodiment, as shown in FIGS. 5A and 5B, a mark (protrusion-state acknowledgement section, state recognition section) 45 is provided on the distal end side of the treatment section 12. It is advisable that the mark 45 be formed of a paint, a rubber covering, a print, or a characteristic shape of the movable section 10 (particular joint, logo mark, or the like).

Furthermore, in this embodiment, when the operator O confirms that the mark 45 on the treatment section 12 is in an endoscopic image displayed on the monitor 5, the operator O performs input using the input section (not shown in the figure) provided in the first operating section 23 of the operation input section 2, thereby causing the control unit 4 to initialize the rotational angles of the encoder 43 and the treatment section 12 and to advance the slider 19 by a preset length corresponding to the distance from the position at which the mark 45 is displayed on the monitor 5 to a position at which the entire movable section 10 protrudes towards the distal end side from the channel 8. Thereafter, when the slider 19 is disposed at the position after the slider 19 has advanced by the preset length, the control unit 4 operates the brake 44 to restrict a retreating motion of the rack gear (restriction mode).

Furthermore, as shown in FIG. 6, when the movable section 10 of the manipulator 3 takes a shape along the longitudinal direction of the flexible section 9 as a result of the operator O operating the first operating section 23 and thereby causing all the joints 26, 27, and 28, constituting the first operating section 23, to take an accommodatable shape (e.g., shape extending in a straight line), the control unit 4 removes the restriction applied by the brake 44 (withdrawable mode).

A method for operating the manipulator system 1 according to this embodiment with the above-described structure will be described below.

Figure 8A:
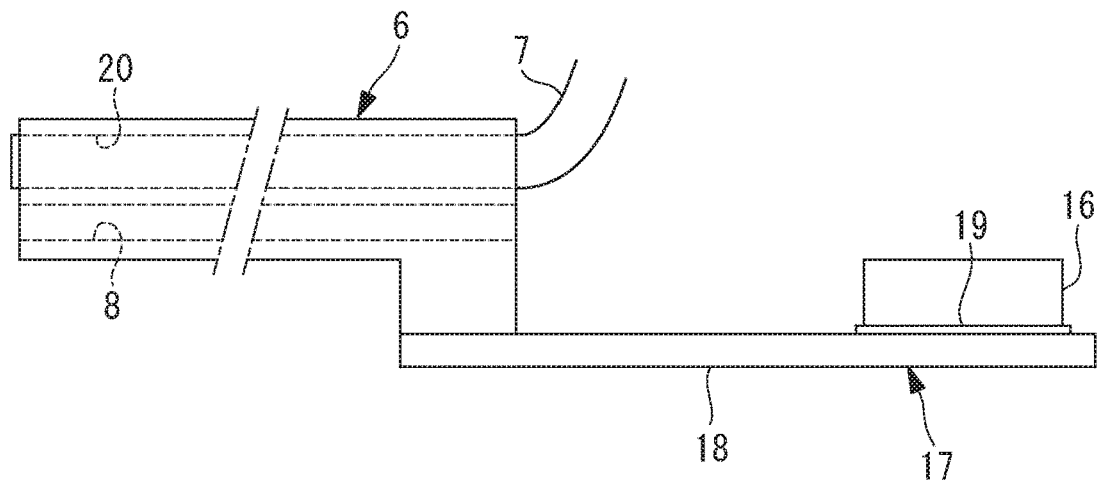
FIG. 8A is a diagram showing a state where the endoscope is inserted into an endoscope channel of the overtube of the manipulator system in FIG. 1.

When an affected area in the body of the patient P is to be treated by using the manipulator system 1 according to this embodiment, the endoscope 7 and the overtube 6 are inserted into the body cavity of the patient P in a state where the endoscope 7 is inserted in the endoscope channel 20 of the overtube 6, as shown in FIG. 8A, and then an image acquired by the endoscope 7 is displayed on the monitor 5.

Figure 9:
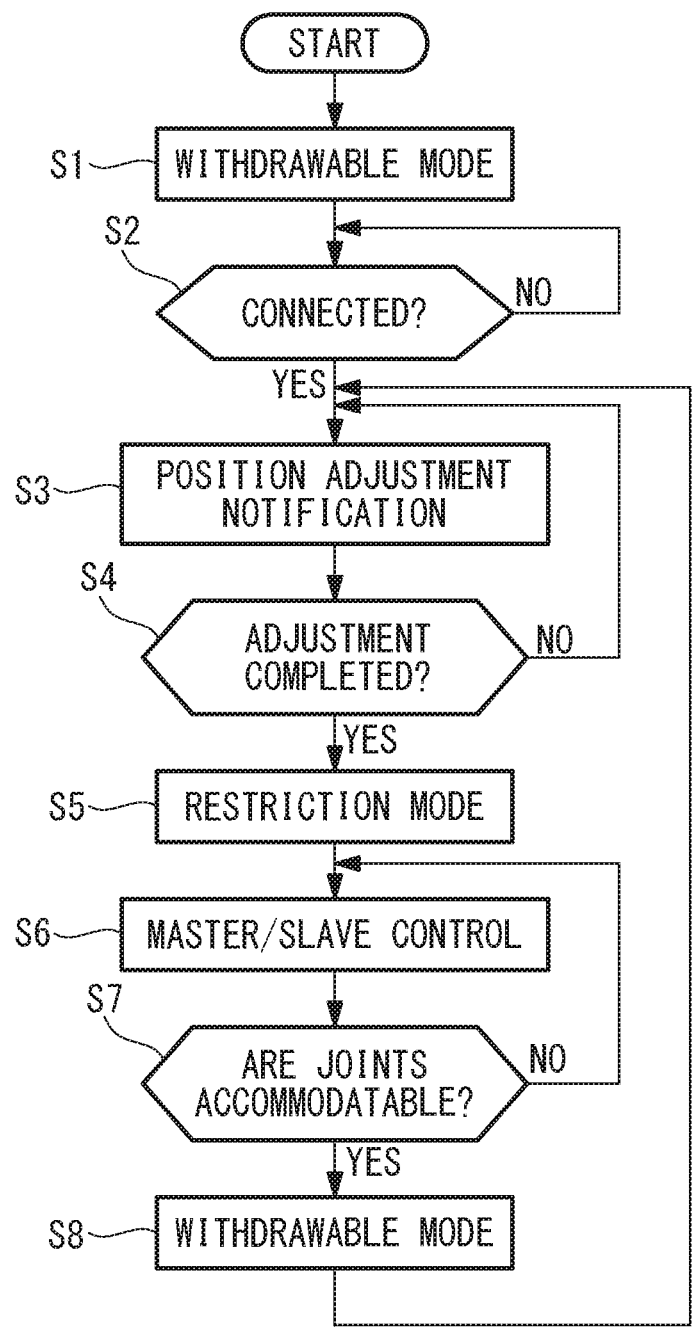
FIG. 9 is a flowchart for illustrating a method for operating the manipulator system in FIG. 1.

As shown in FIG. 9, the control unit 4 removes the restriction applied by the restricting section 42, thereby achieving the withdrawable mode (step S1).

Figure 8B:
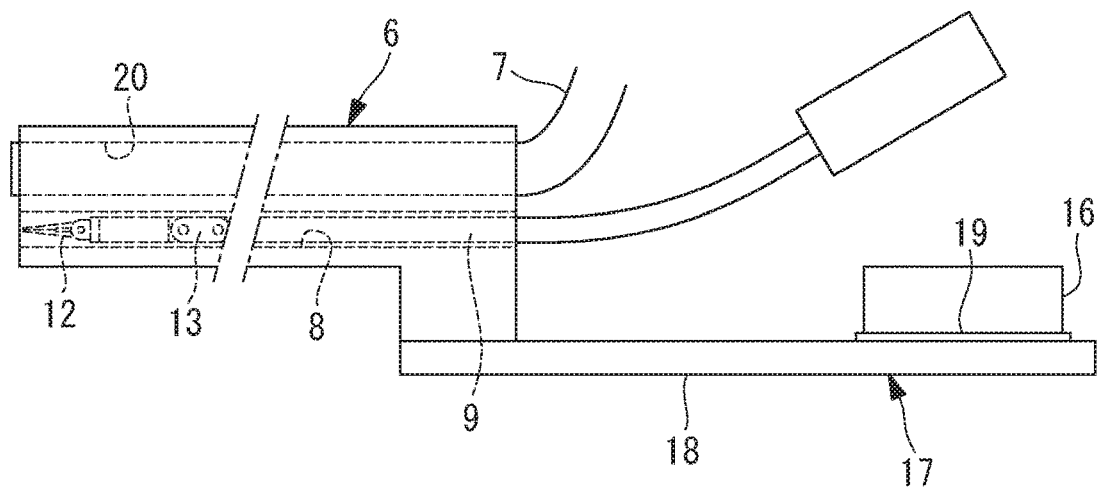
FIG. 8B is a diagram showing a state where a manipulator is inserted into a manipulator channel of the overtube of the manipulator system in FIG. 1.

Thereafter, as shown in FIG. 8B, the slider 19 of each of the advancing/retreating mechanisms 17 is placed at the most-retreated position and is restricted by the brake 44, and then the movable section 10 and the flexible section 9 of each of the manipulators 3 are inserted into the body of the patient P via the manipulator channel 8.

Furthermore, if the slider 19 is not placed at the most-retreated position, the operator O is notified on the monitor 5 or by means of sound that he/she should move the slider 19 to that position. At this time, only in a case where the slider 19 is placed at the most-retreated position, detection is performed by a detection unit (not shown in the figure), such as a sensor for outputting a signal, provided in the advancing/retreating mechanism 17 and then a determination is made.

Figure 8C:
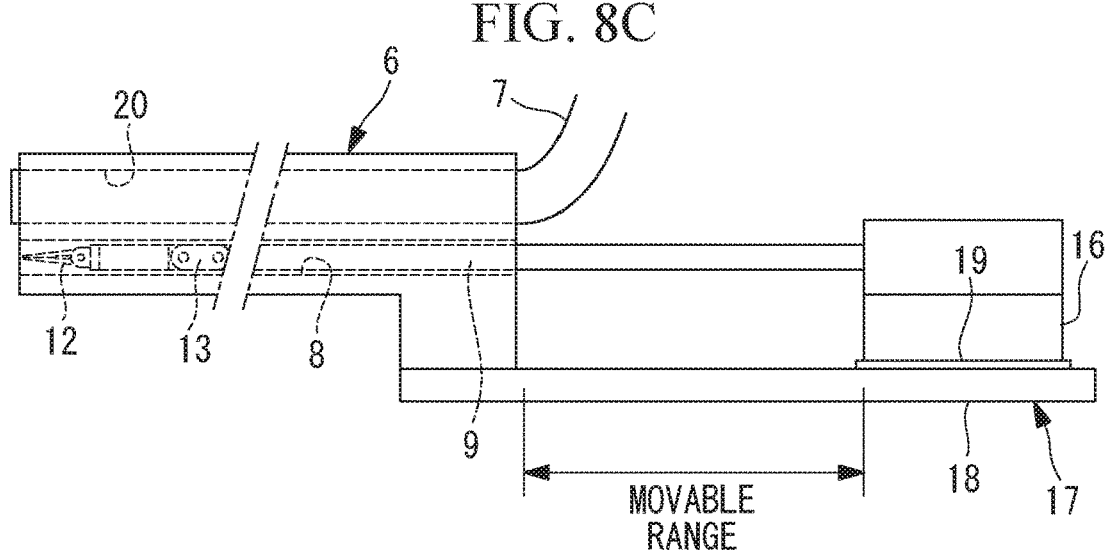
FIG. 8C is a diagram showing a state where a drive unit of the manipulator in FIG. 8B is connected to a motor unit.

Thereafter, when the detection unit detects that the slider 19 is placed at the most-retreated position, connection of the drive unit 11 of the manipulator 3 to the motor unit 16 fixed to the slider 19 of the advancing/retreating mechanism 17 is awaited, as shown in FIG. 8C (step S2). Because the slider 19 is placed at the most-retreated position when the drive unit 11 is connected to the motor unit 16, the entire movable section 10 of the manipulator 3 is completely accommodated in the manipulator channel 8, as shown in FIG. 8C.

Next, the control unit 4 displays a notification on the monitor 5, requiring that the advance/retreat position of the manipulator 3 be adjusted using the slider 19 of the advancing/retreating mechanism 17, thereafter removing the restriction applied by the brake 44.

Accordingly, the operator O applies a force in a direction for advancing the slider 32 to which the arm rest pedestal 30 of the second operating section 24 is fixed. The slider 32 moves in the direction of the applied force, and the amount of linear movement is converted by the first rack and pinion mechanism 37 into a rotational angle.

The amount of linear movement converted into the rotational angle of the first rack and pinion mechanism 37 is transmitted to the second rack and pinion mechanism 38 via the pulley 39 and the belt 41 and is converted into the amount of linear movement of the slider 19 of the advancing/retreating mechanism 17. Because the motor unit 16 is fixed to the slider 19 of the advancing/retreating mechanism 17, the drive unit 11, the flexible section 9, and the movable section 10 connected to the motor unit 16 are made to move along the longitudinal direction of the flexible section 9 in an integrated fashion. By doing so, the treatment section 12 located at the distal end of the movable section 10 is advanced manually.

When the movement of the manipulator 3 performed by the operator O is continued, the movable section 10 provided at the distal end of the manipulator 3 is made to protrude from the distal end of the manipulator channel 8 of the overtube 6. While checking, on the monitor 5, the image acquired by the endoscope 7, the operator O continues to advance the slider 32 of the second operating section 24.

Thereafter, when the treatment section 12 is protruded from the distal end of the manipulator channel 8 as shown in FIG. 5A, the mark 45 provided on the manipulator 3 is displayed on the monitor 5 as shown in FIG. 5B. By doing so, the operator O can recognize that the treatment section 12 is protruded from the distal end of the manipulator channel 8 (state acknowledgement step S3).

Thereafter, it is determined whether or not position adjustment is completed (step S4). When it is determined that adjustment is not completed, the operator O is notified, on the monitor 5, that he/she should carry out position adjustment again. When the operator O performs input, with the input section of the first operating section 23, to indicate that he/she has recognized the mark 45 and it is determined that position adjustment is completed, the encoder 43 is initialized. Note that because the movable section 10 is located in the overtube 6 at this time, the movable section 10 cannot be operated.

When the operator O performs input to indicate that he/she has recognized the mark 45, the control unit 4 advances the slider 19 by a preset length corresponding to the distance from the position at which the mark 45 is displayed on the monitor 5 to a position at which the entire movable section 10 protrudes towards the distal end side from the channel 8 (the operator O may advance the slider 19). When it is detected that the slider 19 is placed at the position after the slider 19 has advanced by the preset length, the restriction mode, in which further movement of the manipulator 3 towards the retreating direction from that initial position is restricted by the brake 44, is entered (restriction step S5). Note that at this time, the control unit 4 starts master/slave control for operatively associating the operation input section 2 with the manipulator 3 (step S6).

Alternatively, master/slave control may be automatically started as soon as the manipulator system 1 detects that the slider 19 is placed at the advanced position. Alternatively, the manipulator system 1 may wait until an operation (e.g., a switch press in the operation input section 2, a button press on the screen, or the like) is received from the operator O, so that master/slave control may be automatically started as soon as the manipulator system 1 detects such an operation.

In order to operate the operation input sections 2 in this state, the operator O grips the distal end portions 29 of the first operating sections 23 with both hands, as shown in FIG. 4, and rests his/her arms on the arm rest pedestals 30 of the second operating sections 24.

When the distal end portion 29 of a first operating section 23 gripped by the operator O is moved with the force of his/her palm or fingers, the displacement is detected by the sensor provided in each of the joints 26, 27, and 28 and is transmitted to the control unit 4 as an electrical signal. In the control unit 4, an electrical motion command for moving the joints 13, 14, and 15 of the movable section 10 so as to correspond to the angles of the respective joints 26, 27, and 28 detected by the sensors is calculated and supplied to the motor of the motor unit 16 connected to each of the joints 13, 14, and 15. By doing so, the distal end position of the treatment section 12 provided at the distal end of the movable section 10 is electrically driven with high precision as instructed with the palm or fingers.

According to the manipulator system 1 of this embodiment, the brake 44 is not engaged when the movable section 10 is driven from the accommodation state, where the movable section 10 is accommodated in the manipulator channel 8 of the overtube 6, to the treatment state, where the movable section 10 is made to protrude from within the manipulator channel 8 as a result of the slider 32 of the second operating section 24 being advanced, thereby allowing the operator O to freely advance and retreat the arm rest pedestal 30 without being restricted in terms of movement.

On the other hand, after it has been recognized by means of the endoscopic image displayed on the monitor 5 that the entire movable section 10 protrudes from the manipulator channel 8 and input has been performed with the input section to confirm this, the rotational angles of the encoder 43 and treatment section 12 are initialized, and when the encoder 43 is at the initial position, the brake 44 is engaged, preventing the arm rest pedestal 30 from any further retreating motion towards the proximal end side.

Once the movement of the arm rest pedestal 30 is restricted, the operator O cannot further retreat the slider 32 and hence can recognize that the movable section 10 is being driven from the protrusion state to the accommodation state. Therefore, it is possible to prevent the movable section 10 from being withdrawn into the manipulator channel 8 as a result of the operator O unconsciously retreating the arm rest pedestal 30 too much.

More specifically, in the restriction mode, the movable section 10 can be freely moved during treatment without being subjected to any restriction, except that further retreating motion is restricted by the brake 44 when the slider 32 of the arm rest pedestal 30 is retreated to the initial position. Therefore, there is an advantage in that it is possible to prevent the joints 13, 14, and 15 of the movable section 10 from being forcibly withdrawn into the manipulator channel 8 in a curved state, thus preventing the distal end of the movable section 10 from moving in an unintended direction and also preventing an excessive load for forcing the curved joints 13, 14, and 15 of the movable section 10 into a straight shape from being applied to the joints 13, 14, and 15.

Furthermore, when the operator O deliberately drives the movable section 10 into the accommodation state, he/she changes each of the joints 26, 27, and 28, constituting the first operating section 23, into an accommodatable shape, as shown in FIG. 6. The accommodatable shape is, for example, a straight shape (step S7). By doing so, each of the joints 13, 14, and 15, constituting the movable section 10, takes a shape along the longitudinal direction of the flexible section 9, and hence the control unit 4 ceases the engagement of the brake 44 (step S8, withdrawable mode). By doing so, the operator O can retreat the slider 32 and accommodate the movable section 10 in the manipulator channel 8 comfortably.

Although the mark 45 is provided on the distal end side of the treatment section 12 in the manipulator system 1 according to this embodiment, instead of this, it is also acceptable to provide an object at a position closer to the proximal end side than the movable section 10 is such that the object is disposed in the field of view of the endoscope 7 in a state where the entire movable section 10 protrudes from the channel 8 towards the distal end side, as shown in FIG. 10A.

By doing so, the operator O can visually recognize that the entire movable section 10 protrudes from the distal end of the manipulator channel 8 by means of the mark 45 in the endoscopic image displayed on the monitor 5, and thereby the control unit 4 can start master/slave control for operatively associating the operation input section 2 with the manipulator 3 without the operator O having to operate the advancing/retreating mechanism 17.

Alternatively, master/slave control may be automatically started as soon as the manipulator system 1 detects that the slider 19 is placed at the advanced position. Alternatively, the manipulator system 1 may wait until an operation (e.g., a switch press in the operation input section 2, a button press on the screen, or the like) is received from the operator O, so that master/slave control may be automatically started as soon as the manipulator system 1 detects such an operation.

In addition, as shown in FIG. 10B, a recessed section (state recognition section) 46 shaped like a circumferential groove may be provided in the inner surface of the manipulator channel 8, and a protruding section (engaging section, state recognition section) 47 that is brought into engagement with the recessed section 46 when the entire movable section 10 protrudes from the distal end of the manipulator channel 8 may be provided on the external surface of the manipulator 3. The protruding section 47 is, for example, an elastically deformable ring, such as rubber.

Figure 10C:
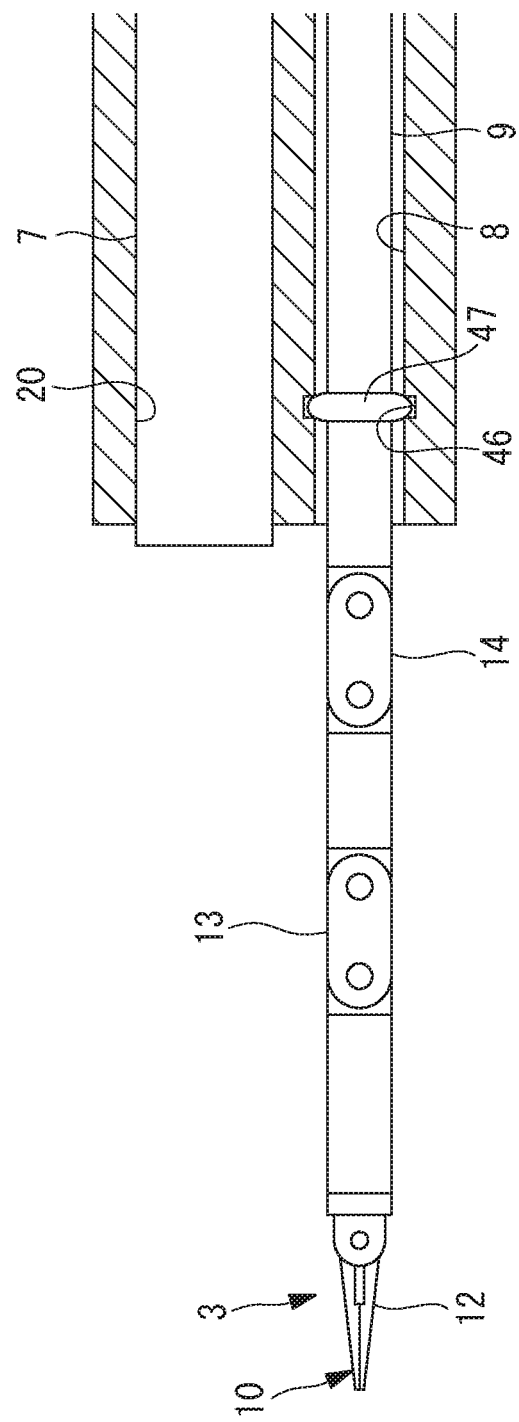
FIG. 10C is a partial longitudinal sectional view showing that a protrusion state, where the entire movable section protrudes from the distal end of the overtube, is recognized with the state recognition section in FIG. 10B.

When the protruding section 47 coincides with the recessed section 46 as a result of the movement of the manipulator 3 as shown in FIG. 10C, the protruding section 47 is restored to an enlarged shape and is brought into engagement with the recessed section 46. By doing so, the operator O can recognize, by means of the sense of force (clicking sensation), that the entire movable section 10 protrudes from the distal end of the manipulator channel 8.

The protruding section 47 may be provided on the inner surface of the manipulator channel 8, and the recessed section (engaging section) 46 that is brought into engagement with the protruding section 47 may be provided in the external surface of the manipulator 3.

In addition, instead of the operator O performing input by using the input section provided at the distal end portion 29 of the operation input section 2 to indicate that the operator O has recognized the mark 45 on an endoscopic image, the operator O may be made to perform input by operating a button displayed on the monitor 5 via the GUI.

Figure 11A:
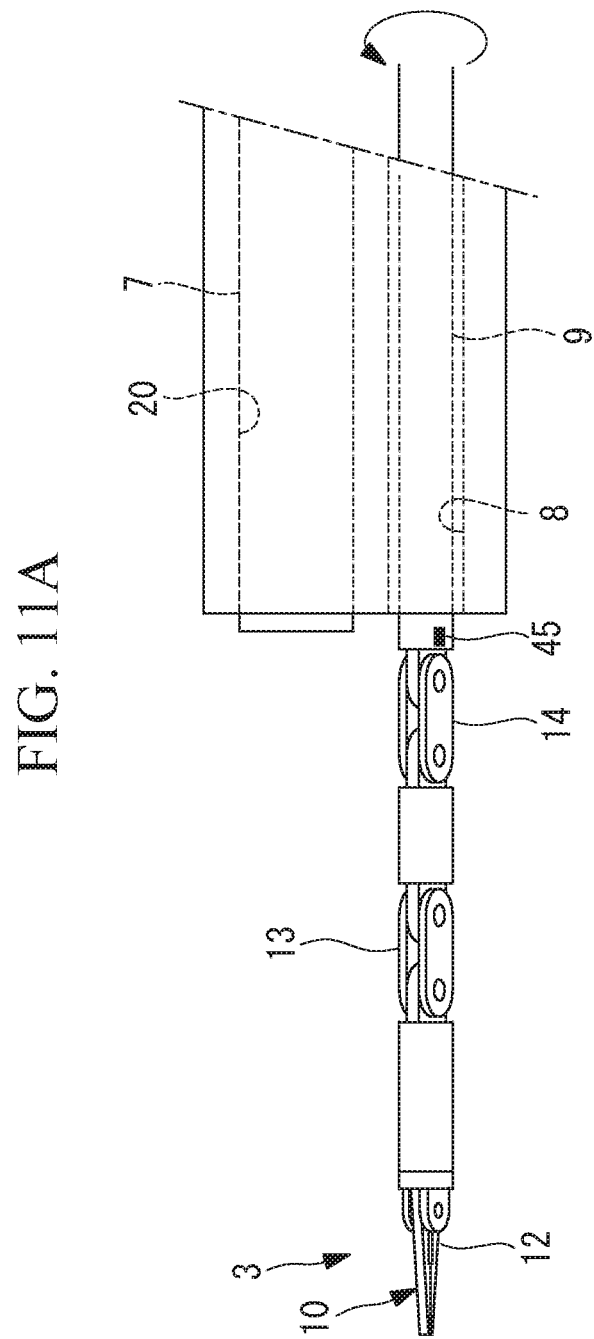
FIG. 11A is a diagram showing a modification of the mark, serving as the state recognition section, of the manipulator system in FIG. 1.
Figure 11B:
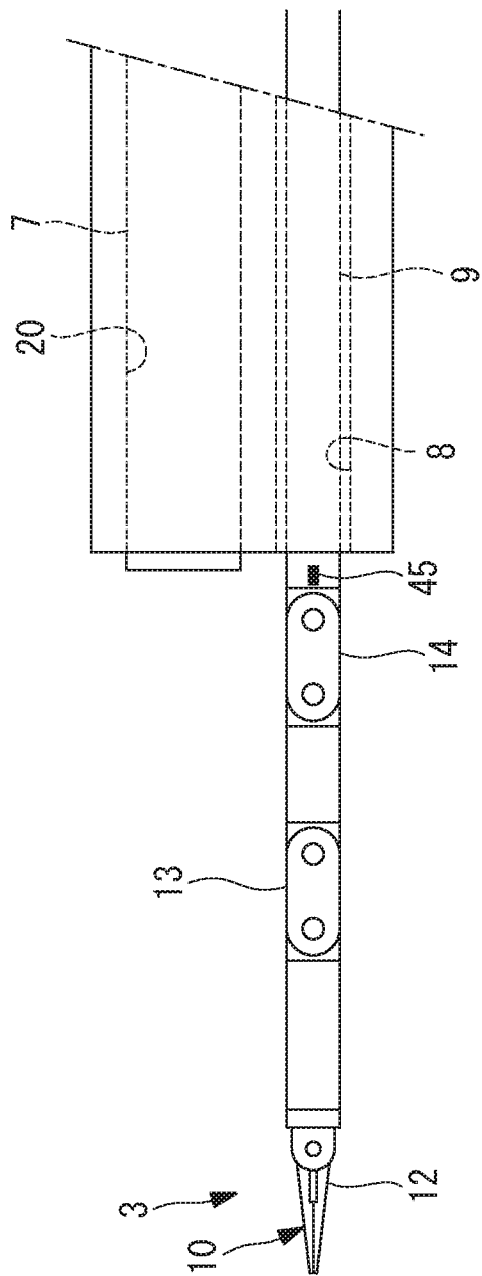
FIG. 11B is a diagram showing a state where the mark is disposed at the center by rotating the manipulator about the longitudinal axis of a flexible section with respect to the state in FIG. 11A.

Furthermore, although the operator O is made to recognize that the entire movable section 10 protrudes from the distal end of the manipulator channel 8 by means of the mark 45 appearing on an endoscopic image, in addition to this, the rotation of the movable section 10 about the longitudinal axis of the flexible section 9 may also be initialized by using the mark 45. For example, the rotational position of the movable section 10 may be adjusted by using an object with which a position in the circumferential direction can be identified, such as the mark 45 that is present only at a portion in the circumferential direction as shown in FIGS. 11A and 11B, so that the mark 45 appears in the front on the endoscopic image as shown in FIG. 11B.

Figure 12:
FIG. 12 is a diagram showing one example of a GUI screen for allowing a user to execute the rotational movement in FIG. 11B.
Figure 12:

If the manipulator 3 has a rotational joint that is closer to the proximal end side than the movable section 10 is, a button as shown in FIG. 12 may be displayed via the GUI to prompt the operator O to perform a rotational operation and a confirmation operation. The confirmation operation in this case may be that same as a confirmation operation for initializing the encoder 43.

In addition, instead of making the operator O recognize that the entire movable section 10 protrudes from the distal end of the manipulator channel 8 and perform input to indicate this fact via the input section, the control unit 4 may include: a shape estimation unit (not shown in the figure) for estimating the curved shape of the overtube 6; and an advance/retreat-amount calculation unit (not shown in the figure) for calculating, on the basis of the estimated curved shape, the amount of advance/retreat and the amount of rotation in the longitudinal direction of the drive unit 11 that achieve a state where the entire movable section 10 protrudes from the distal end of the manipulator channel 8.

A calculation method on the basis of the curved shape can be illustrated in FIG. 13 and represented by the expression below:

$$\Delta d = \pi \times (R_{out} - R_{in}) \times \theta / 180$$

Figure 13:
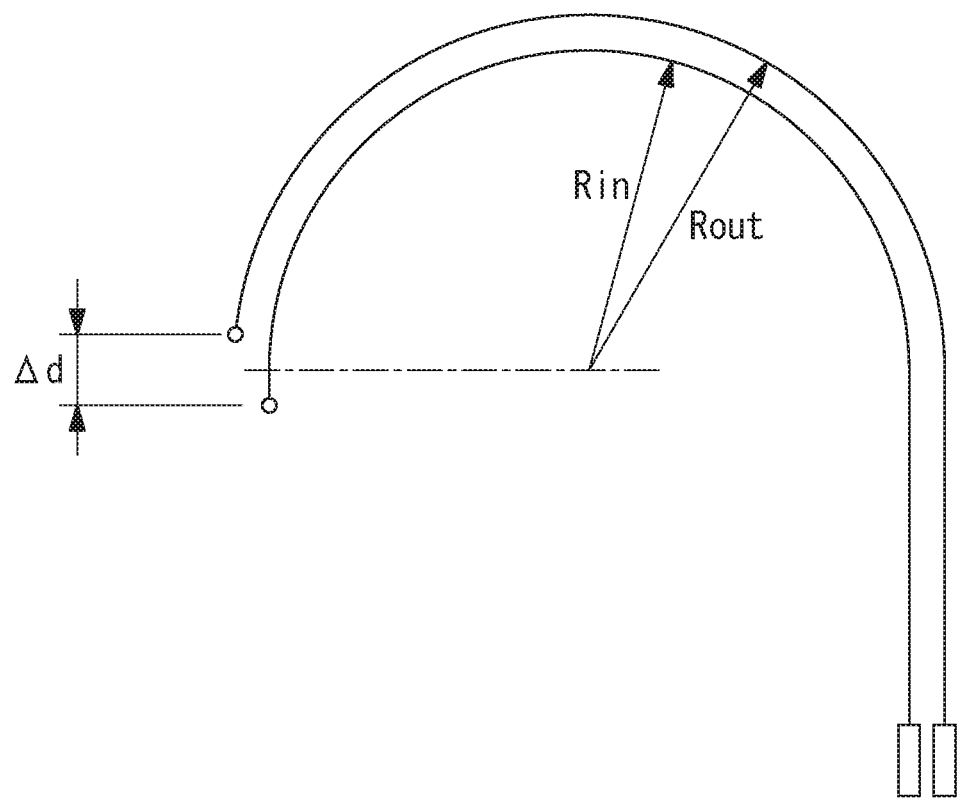
FIG. 13 is a diagram for illustrating a calculation method for calculating the amount of advance/retreat of the drive unit on the basis of a curved shape of the overtube, said amount for achieving a state where the entire movable section protrudes from the distal end of the manipulator channel.

Here, $\Delta d$ is the route difference between the two manipulator channels 8 in a case where the two manipulator channels 8 are arranged side by side in the radial direction of the curved shape, and $\theta$ is the angle of the curved portion ($\theta = 180°$ in the example shown in FIG. 13).

In the present example, an example calculation is shown for the difference between inner and outer curves of the two manipulator channels 8. Besides this example, the route length varies in the curve direction depending on the distance between the central axes of a manipulator channel 8 and the insertion section 6. This amount of change is represented by the expression below:

$$\Delta d' = \pi \times \Delta r \times \theta / 180$$

Here, $\Delta r$ is the distance between the central axis of the insertion section 6 and the central axis of the manipulator channel 8 in the direction in which the insertion section 6 is curved.

In addition, in a case where a curved portion is formed at the distal end of the insertion section 6, the route length from the proximal end to the distal end of the flexible section 6 (manipulator channel 8) can be obtained by performing the same calculation for the curve direction and angle.

In addition, the control unit 4 may store, in a memory unit (not shown in the figure), identification information of a site to be treated and the curved shape in an associated manner, so that when the operator O, prior to treatment, inputs the identification information of the site to be treated by using an identification information input section (not shown in the figure), the control unit 4 can calculate the amount of advance/retreat and the amount of rotation in the longitudinal direction of the drive unit 11 on the basis of the curved shape that has been read out from the memory unit.

Alternatively, the overtube 6 may be provided with a shape sensor, such as a strain gage, an optical fiber sensor, or a magnetic sensor, so that the amount of advance/retreat and the amount of rotation in the longitudinal direction of the drive unit 11 can be calculated on the basis of the curved shape of the overtube 6 detected by the shape sensor, said amounts for achieving a state where the entire movable section 10 protrudes from the distal end of the manipulator channel 8.

Figure 14:
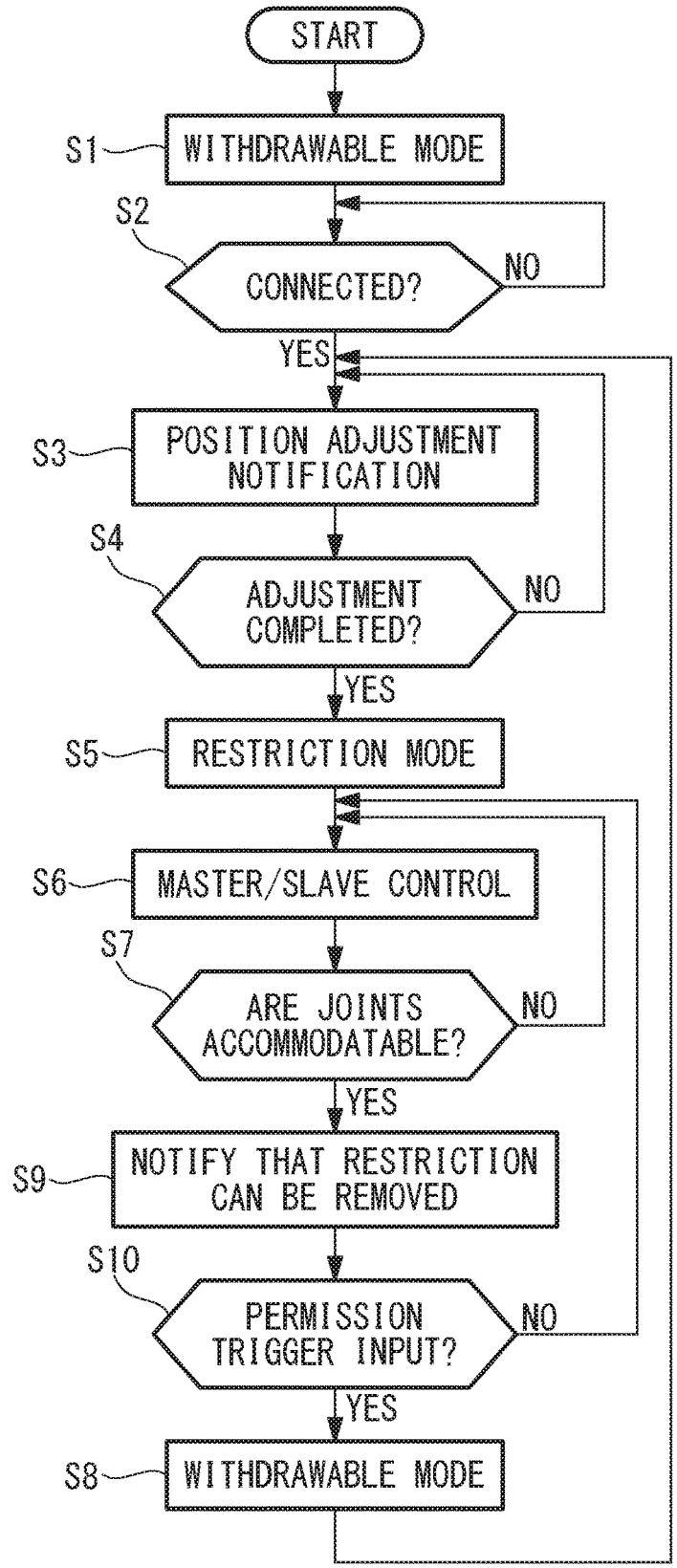
FIG. 14 is a flowchart for illustrating a modification of the method for operating the manipulator system in FIG. 9.

In this embodiment, the control unit 4 removes the restriction applied by the brake 44 when the movable section 10 takes an accommodatable shape. Instead of this, as shown in FIG. 14, when the movable section 10 takes an accommodatable shape, the control unit 4 may report that the restriction can be removed (step S9), so that the operator O may input a withdrawing permission trigger in this reported state (step S10) to remove the restriction applied by the brake 44.

In addition, as shown in FIG. 15, in the restriction mode where a withdrawing motion towards the proximal end side across the initial position is restricted by the brake 44, the operator O may input a withdrawing trigger (step S11) to make the control unit 4 control the movable section 10 so as to be driven into an automatically withdrawable shape (step S12), thus shifting to the withdrawable mode. After having driven the movable section 10 into a withdrawable shape, the control unit 4 may move the slider 19 of the advancing/retreating mechanism 17 to the position on the most proximal end side.

In addition, the control unit 4 may control the movable section 10 to drive the movable section 10 into an automatically withdrawable shape only while the operator O holds the withdrawing trigger. In this case, when the operator O releases the withdrawing trigger, the motion of the movable section 10 performed by the control unit 4 stops.

Alternatively, the restriction applied by the brake 44 may be removed when it is detected that the operator O has disconnected the drive unit 11 from the motor unit 16. As a result of the connection between the motor unit 16 and the drive unit 11 having been released, the movable section 10 is placed in a state where it is moved by an external force, and hence the manipulator 3 can be extracted from the channel 8 of the overtube 6, as long as the brake 44 is released.

Alternatively, instead of shifting to the withdrawable mode by using the withdrawing trigger, the withdrawable mode may be achieved when a request for adjusting the position of the overtube 6 is detected.

In addition, although the present invention has been described by way of an example where the channel 8 into which the manipulator 3 is inserted is provided in the overtube 6, the present invention may be applied to a case where the manipulator 3 is introduced via a channel provided in the insertion section of the endoscope 7.

As a result, the above-described embodiment also leads to the following aspects.

One aspect of the present invention is a manipulator system including: a manipulator including an elongated flexible section, a movable section provided at a distal end of the flexible section, and a drive unit that is provided at a proximal end of the flexible section and that drives the movable section; an insertion section having a channel through which the manipulator passes and having flexibility; an advancing/retreating section that advances/retreats the manipulator in a longitudinal direction of the flexible section and that causes the movable section of the manipulator to protrude from, and to be withdrawn into, a distal end of the channel; a protrusion-state acknowledgement section for acknowledging a protrusion state in which the entire movable section protrudes from the distal end of the channel; and a restricting section that, when the protrusion state is acknowledged with the protrusion-state acknowledgement section, restricts further retreating motion of the drive unit performed by the advancing/retreating section.

According to this aspect, the insertion section having flexibility is inserted into, for example, the body of a patient while the insertion section is curved so that the distal end thereof is disposed to face an affected area, and thereafter the manipulator is advanced through the channel of the insertion section by advancing the advancing/retreating section to which the drive unit is attached, thus causing the movable section provided at the distal end thereof to protrude from the distal end of the channel. When it is acknowledged with the protrusion-state acknowledgement section that the entire movable section protrudes from the distal end of the channel, the advancing/retreating section is restricted by the working of the restricting section so that the drive unit does not retreat from that position thereof.

More specifically, because the movable section is prevented from being partially withdrawn into the channel after restriction has been activated by the restricting section, an operator can freely operate the movable section, the entirety of which has been protruded from the distal end of the channel, without any restriction. By doing so, it is possible to prevent the movable section from being withdrawn into the channel while in a curved state or the movable section from being partially withdrawn into the channel, thereby preventing the motion of the movable section itself from being restricted when the operator does not intend to do so.

In the above-described aspect, the protrusion-state acknowledgement section may include a state recognition section for allowing an operator to recognize whether or not the protrusion state is achieved and an input section that, when the protrusion state is recognized with the state recognition section, allows the operator to input this fact.

By doing so, the operator, who has recognized with the state recognition section that the entire movable section has protruded from the distal end of the channel, inputs this fact with the input section, whereby the restricting section restricts the advancing/retreating section so that the drive unit does not retreat from that position.

In addition, the above-described aspect may include: an image acquisition unit for acquiring an image of a distal end side of the insertion section; and a display unit for displaying the image acquired by the image acquisition unit, wherein the state recognition section may be a mark provided at a position, on the manipulator, disposed within a field of view of the image acquisition unit when the movable section is in the protrusion state.

By doing so, when the manipulator is advanced through the channel and the entire movable section is made to protrude from the distal end of the channel, the mark provided on the manipulator is disposed in the field of view of the image acquisition unit, and the image acquired by the image acquisition unit is displayed on the display unit. As a result, with the image displayed on the display unit, the operator can easily and visually recognize that the entire movable section of the manipulator has protruded from the distal end of the channel.

In addition, in the above-described aspect, the state recognition section may include a recessed section or a protruding section provided in the channel and an engaging section that is provided on an external surface of the manipulator and that, when the movable section is in the protrusion state, is disengageably brought into engagement with the recessed section or the protruding section.

By doing so, when the manipulator is advanced through the channel and the entire movable section is made to protrude from the distal end of the channel, the engaging section provided on the external surface of the manipulator is brought into engagement with the recessed section or the protruding section provided in the channel. As a result, the operator can easily recognize, by means of the sense of force, that the entire movable section of the manipulator has protruded from the distal end of the channel. Furthermore, once the retreating motion of the drive unit has been restricted by the restricting section, the recessed section or the protruding section is disengaged from the engaging section, thereby allowing an advance motion of the drive unit and free motion of the movable section.

In addition, in the above-described aspect, the protrusion-state acknowledgement section may include a shape estimation unit for estimating a curved shape of the insertion section and an advance/retreat-amount calculation unit for calculating, on the basis of the curved shape estimated by the shape estimation unit, the amount of advance/retreat of the drive unit performed by the advancing/retreating section, said amount for bringing the movable section into the protrusion state.

By doing so, if the curved shape of the insertion section is estimated in advance by the shape estimation unit, the amount of advance/retreat of the drive unit for causing the entire movable section to protrude from the distal end of the channel can be calculated by the advance/retreat-amount calculation unit, the protrusion state is acknowledged on the basis of the calculation result, and restriction using the restricting section can be performed.

In addition, in the above-described aspect, the shape estimation unit may include a sensor provided in the insertion section.

By doing so, the curved shape of the insertion section can be easily estimated by the sensor provided in the insertion section.

In addition, in the above-described aspect, the shape estimation unit may include a memory unit for storing, in an associated manner, identification information of a site in a body cavity and the curved shape in a state where the insertion section is inserted up to the site and an identification information input section for allowing the identification information to be input.

By doing so, when the operator inputs, with the identification information input section, the identification information of the site to be treated in the body cavity, the curved shape of the insertion section stored in the memory unit in an associated manner is read out, thereby making it possible to easily estimate the curved shape of the insertion section.

In addition, another aspect of the present invention is a method for operating a manipulator system, the method including: a state acknowledgement step of acknowledging, in a state where a manipulator including a movable section at a distal end of an elongated flexible section and a drive unit, at a proximal end thereof, for driving the movable section is inserted in a channel of an insertion section in which a curved shape is set and that has flexibility, whether or not a protrusion state in which the entire movable section protrudes from a distal end of the channel is achieved; and a restriction step of restricting a retreating motion of the drive unit from the position thereof when it is acknowledged in the state acknowledgement step that the protrusion state is achieved.

The present invention affords an advantage in that the position of a manipulator protruding from the distal end of an insertion section can be detected with high accuracy, thereby making it possible to prevent the manipulator from being withdrawn into a channel while the manipulator remains in a curved shape and to prevent the manipulator accommodated in the channel from erroneously working.

REFERENCE SIGNS LIST

1 Manipulator system
3 Manipulator
6 Overtube (insertion section)
7 Endoscope (image acquisition unit)
8 Channel
9 Flexible section
10 Movable section
11 Drive unit
17 Advancing/retreating mechanism (advancing/retreating section)
42 Restricting section
45 Mark (protrusion-state acknowledgement section, state recognition section)
46 Recessed section (state recognition section, engaging section)
47 Protruding section (state recognition section, engaging section)
S3 State acknowledgement step
S5 Restriction step

The invention claimed is:

1. A manipulator system comprising:
   a manipulator including a movable section provided at a distal end of a flexible section, wherein the movable section comprises at least one joint;
   an insertion section having a proximal end, a distal end and a channel formed between the proximal end of the insertion section and the distal end of the insertion section, the channel being configured to receive the manipulator from the proximal end of the insertion section to the distal end of the insertion section; and
   a controller configured to;
      receive a signal indicating whether a predetermined portion of the manipulator protrudes from the distal end of the insertion section;
      based on the received signal, control a mechanism to move the manipulator distally to a position where an entirety of the movable section protrudes from the distal end of the insertion section; and
      control a brake to restrict a motion of the manipulator from moving proximally from the position.

2. The manipulator system according to claim 1, wherein the predetermined portion comprises a distal end side of the movable section.

3. The manipulator system according to claim 1, wherein the receiving comprises receiving an operation input indicating an operation of the manipulator.

4. The manipulator system according to claim 1, further comprising:
   an endoscope configured to acquire an image of a further distal end side than a distal end of the insertion section, wherein the image containing a mark provided on a distal end side of the movable section, the mark being configured to indicate that the movable section protrudes from the distal end of the insertion section,
   wherein the receiving comprises receiving the signal from a user input based on the observation.

5. The manipulator system according to claim 1, wherein the channel comprises one of a recessed section or a protruding section, and an external surface of the manipulator comprises an other of the recessed section and the protruding section, the recessed section being configured to engage with the protruding section when the movable section protrudes from the distal end of the insertion section at the position.

6. The manipulator system according to claim 1, wherein:
the signal estimates a curved shape of the insertion section; and
the controller calculates, on a basis of the estimated curved shape, an amount of advance/retreat of the manipulator, the amount being such that the predetermined portion of the manipulator protrudes from the distal end of the tube.

7. The manipulator system according to claim 6, wherein the controller further comprising a memory that stores, in an associated manner, identification information of a site in a body cavity and the curved shape in a state where the insertion section is inserted up to the site and an identification information input that allows the identification information to be input.

8. The manipulator system according to claim 1, wherein the controller is further configured to remove the control to restrict the motion of the manipulator from moving proximally from the position when the movable section is in a linear shape.

9. The manipulator system according to claim 1, wherein, prior to the restriction of the motion of the manipulator from moving proximally from the position, the controller is further configured to restrict master-slave control of the movable section, and subsequent to the restriction of the motion of the manipulator from moving proximally from the position, the controller is further configured to, permit master-slave control of the movable section based on a master input.

10. The manipulator system according to claim 1, wherein the controller is configured to further control the manipulator based on a determined shape of the insertion section.

11. The manipulator system according to claim 1, wherein the controller being further configured to remove the restriction when the movable section takes a predetermined shape.

12. The manipulator system according to claim 11, wherein the predetermined shape is a straight shape.

13. The manipulator system of claim 1, further comprising an actuator operatively connected to the at least one joint for driving the at least one joint.

14. The manipulator system of claim 1, further comprising the mechanism configured to advance/retract the manipulator with respect to the insertion section.

15. The manipulator system of claim 1, further comprising the brake configured to restrict the motion of the manipulator from moving proximally.

16. A method for operating a manipulator system, the method comprising:
in a state where a manipulator including a movable section at a distal end of an elongated flexible section and a driver, at a proximal end thereof, for driving the movable section is inserted in a channel of an insertion section in which a curved shape is set and that has flexibility, receiving a signal indicating that a predetermined portion of the movable section protrudes from a distal end of the channel;
based on the received signal, moving the manipulator distally to a position where an entirety of the movable section protrudes from the distal end of the insertion section; and
controlling a brake to restrict motion of the manipulator from moving proximally form the position.

17. A controller for controlling a manipulator system that comprises a manipulator having a movable section provided at a distal end, a tube into which the manipulator is insertable, and a slider to which the manipulator is attachable, the manipulator system causing the movable section to protrude from, and to be withdrawn into, the tube by advancing/retreating the slider, wherein the controller is configured to:
receive a signal indicating whether a predetermined portion of the manipulator protrudes from a distal end of the tube,
based on the received signal, control the slider to move the manipulator distally to a position where an entirety of the movable section protrudes from the distal end of the insertion section; and
based on the received signal, control the slider to restrict a motion of the manipulator from moving proximally from the position.

18. The controller according to claim 17, wherein the signal indicates a detected curved shape of the tube,
the controller calculates an amount of advance/retreat of the slider to indicate whether the predetermined portion of the manipulator protrudes from the distal end of the tube, on a basis of the detected curved shape.

19. The controller according to claim 17, further comprising a memory that stores an identification information of a site in a body cavity and a curved shape of the tube in a state where the tube is inserted up to the site in association with each other,
wherein the predetermined portion of the manipulator is indicated as protruding from the distal end of the tube by calculating an amount of advance/retreat of the slider with which the predetermined portion of the manipulator protrudes from the distal end of the tube, on a basis of the curved shape read from the memory in accordance with an input of the identification information.

20. A manipulator system comprising:
a manipulator including a movable section provided at a distal end of a flexible section, wherein the movable section comprises at least one joint;
an insertion section having a proximal end, a distal end and a channel formed between the proximal end of the insertion section and the distal end of the insertion section, the channel being configured to receive the manipulator from the proximal end of the insertion section to the distal end of the insertion section; and
a controller configured to;
receive a signal indicating whether a predetermined portion of the manipulator protrudes from the distal end of the insertion section; and
when the predetermined portion is determined to protrude from the distal end of the insertion section, control a brake to restrict a motion of the manipulator from moving proximally.

21. The manipulator system according to claim 20, wherein, prior to the restricting, the controller controls the manipulator to move the manipulator distally to a position and the controller controls the brake to restrict the motion of the manipulator from moving proximally from the position.

22. The manipulator system according to claim 21, wherein the position is where an entirety of the movable section protrudes from a distal end of the insertion section.

* * * * *